US011827889B2

(12) United States Patent
Kochenderfer

(10) Patent No.: US 11,827,889 B2
(45) Date of Patent: *Nov. 28, 2023

(54) CHIMERIC ANTIGEN RECEPTORS TARGETING B-CELL MATURATION ANTIGEN

(71) Applicant: The United States of America, as represented by the Secretary, Department of Health and Human Services, Bethesda, MD (US)

(72) Inventor: James N. Kochenderfer, Bethesda, MD (US)

(73) Assignee: The U.S.A., as represented by the Secretary, Department of Health and Human Services, Bethesda, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/938,535

(22) Filed: Oct. 6, 2022

(65) Prior Publication Data
US 2023/0030998 A1 Feb. 2, 2023

Related U.S. Application Data

(63) Continuation of application No. 17/745,067, filed on May 16, 2022, which is a continuation of application No. 17/117,368, filed on Dec. 10, 2020, now Pat. No. 11,359,204, which is a continuation of application No. 16/683,524, filed on Nov. 14, 2019, now Pat. No. 10,900,042, which is a continuation of application No. 15/692,473, filed on Aug. 31, 2017, now Pat. No. 10,767,184, which is a continuation of application No. 14/389,677, filed as application No. PCT/US2013/032029 on Mar. 15, 2013, now Pat. No. 9,765,342.

(60) Provisional application No. 61/622,600, filed on Apr. 11, 2012.

(51) Int. Cl.
| | |
|---|---|
| C12N 15/62 | (2006.01) |
| C07K 14/705 | (2006.01) |
| C07K 14/725 | (2006.01) |
| C07K 16/28 | (2006.01) |
| C07K 16/18 | (2006.01) |
| A61K 48/00 | (2006.01) |
| A61K 39/00 | (2006.01) |

(52) U.S. Cl.
CPC .......... *C12N 15/62* (2013.01); *C07K 14/7051* (2013.01); *C07K 14/70503* (2013.01); *C07K 14/70517* (2013.01); *C07K 14/70521* (2013.01); *C07K 14/70578* (2013.01); *C07K 16/18* (2013.01); *C07K 16/2878* (2013.01); *A61K 48/00* (2013.01); *A61K 2039/505* (2013.01); *C07K 2317/73* (2013.01); *C07K 2319/00* (2013.01); *C07K 2319/03* (2013.01)

(58) Field of Classification Search
None
See application file for complete search history.

(56) References Cited

U.S. PATENT DOCUMENTS

| | | | |
|---|---|---|---|
| 4,235,871 A | 11/1980 | Papahadjopoulos et al. | |
| 4,501,728 A | 2/1985 | Geho et al. | |
| 4,837,028 A | 6/1989 | Allen | |
| 5,019,369 A | 5/1991 | Presant et al. | |
| 5,087,616 A | 2/1992 | Myers et al. | |
| 5,122,464 A | 6/1992 | Wilson et al. | |
| 5,464,758 A | 11/1995 | Gossen et al. | |
| 5,770,359 A | 6/1998 | Wilson et al. | |
| 5,814,618 A | 9/1998 | Bujard et al. | |
| 7,112,715 B2 | 9/2006 | Chambon et al. | |
| 9,447,194 B2 | 9/2016 | Jensen | |
| 9,499,629 B2 | 11/2016 | June et al. | |
| 9,765,342 B2 | 9/2017 | Kochenderfer | |
| 10,183,993 B2 * | 1/2019 | Orentas | C12N 15/09 |
| 10,189,903 B2 | 1/2019 | Jensen | |
| 10,550,179 B2 * | 2/2020 | Orentas | C12N 5/0636 |
| 10,738,312 B2 | 8/2020 | Kochenderfer | |
| 10,738,313 B2 | 8/2020 | Kochenderfer | |
| 10,767,184 B2 | 9/2020 | Kochenderfer | |
| 10,815,487 B2 | 10/2020 | Kochenderfer | |
| 10,815,488 B2 | 10/2020 | Kochenderfer | |
| 10,829,556 B2 | 11/2020 | Jensen | |
| 10,829,767 B2 | 11/2020 | Kochenderfer | |
| 10,829,768 B2 | 11/2020 | Kochenderfer | |
| 10,829,769 B2 | 11/2020 | Kochenderfer | |

(Continued)

FOREIGN PATENT DOCUMENTS

| | | |
|---|---|---|
| AU | 2005200008 A1 | 1/2005 |
| CN | 1839201 A | 9/2006 |

(Continued)

OTHER PUBLICATIONS

Granulocyte-Macrophage Colony-stimulating Factor Receptor Subunit Alpha isoform a precursor (*Homo sapiens*) (NCBI Reference Sequence: NP_001155001.1 Mar. 18, 2023) (Year: 2023).*
Adler et al., "Therapeutic Antibodies Against Cancer", 26 *Hematology-Oncology Clinics of North America* 447-81 (2012).
Affidavit of Duncan Hall, Records Request Processor at the Internet Archive (Aug. 31, 2021), with authenticated printouts of the Internet Archive's records of certain files archived at web.archive.org, filed in Petition for Inter Partes Review of U.S. Pat. No. 9,765,342, IPR2021-01484, filed Sep. 9, 2021.
Ahmad et al., "scFv Antibody—Principles and Clinical Application", *Clinical and Developmental Immunology* (2012).

(Continued)

*Primary Examiner* — Peter J Reddig
(74) *Attorney, Agent, or Firm* — LEYDIG, VOIT & MAYER

(57) ABSTRACT

The invention provides an isolated and purified nucleic acid sequence encoding a chimeric antigen receptor (CAR) directed against B-cell Maturation Antigen (BCMA). The invention also provides host cells, such as T-cells or natural killer (NK) cells, expressing the CAR and methods for destroying multiple myeloma cells.

18 Claims, 11 Drawing Sheets

Specification includes a Sequence Listing.

(56) References Cited

U.S. PATENT DOCUMENTS

| | | | |
|---|---|---|---|
| 10,837,019 B2 | 11/2020 | Kochenderfer | |
| 10,844,387 B2 | 11/2020 | Kochenderfer | |
| 10,876,123 B2 | 12/2020 | Kochenderfer | |
| 10,900,042 B2 | 1/2021 | Kochenderfer | |
| 10,925,969 B2 | 2/2021 | Pastan et al. | |
| 11,066,674 B2* | 7/2021 | Kochenderfer | C07K 14/70578 |
| 11,359,204 B2* | 6/2022 | Kochenderfer | C07K 14/70521 |
| 11,377,660 B2* | 7/2022 | Kochenderfer | A61P 35/02 |
| 2003/0012783 A1 | 1/2003 | Kindsvogel | |
| 2003/0157639 A1* | 8/2003 | Barnes | C07K 14/7158 |
| | | | 435/325 |
| 2007/0009518 A1 | 1/2007 | Novobrantseva et al. | |
| 2009/0093024 A1 | 4/2009 | Bowers et al. | |
| 2011/0020343 A1 | 1/2011 | Senter et al. | |
| 2011/0135639 A1 | 6/2011 | Yu et al. | |
| 2012/0148552 A1 | 6/2012 | Jensen | |
| 2013/0280221 A1 | 10/2013 | Schonfeld et al. | |
| 2013/0287748 A1 | 10/2013 | June et al. | |
| 2015/0017141 A1* | 1/2015 | June | C07K 14/70503 |
| | | | 435/325 |
| 2015/0051266 A1 | 2/2015 | Kochenderfer | |
| 2018/0051292 A1 | 2/2018 | Kochenderfer | |
| 2020/0071705 A1 | 3/2020 | Kochenderfer | |
| 2020/0071706 A1 | 3/2020 | Kochenderfer | |
| 2020/0071707 A1 | 3/2020 | Kochenderfer | |
| 2020/0071708 A1 | 3/2020 | Kochenderfer | |
| 2020/0071709 A1 | 3/2020 | Kochenderfer | |
| 2020/0071710 A1 | 3/2020 | Kochenderfer | |
| 2020/0087667 A1 | 3/2020 | Kochenderfer | |
| 2020/0087668 A1 | 3/2020 | Kochenderfer | |
| 2020/0087669 A1 | 3/2020 | Kochenderfer | |
| 2020/0087670 A1 | 3/2020 | Kochenderfer | |
| 2020/0102567 A1 | 4/2020 | Kochenderfer | |
| 2020/0138865 A1 | 5/2020 | Kochenderfer et al. | |
| 2020/0231663 A1* | 7/2020 | Orentas | C12N 5/0638 |
| 2021/0309740 A1 | 10/2021 | Jensen | |
| 2023/0002776 A1 | 1/2023 | Kochenderfer | |

FOREIGN PATENT DOCUMENTS

| | | |
|---|---|---|
| JP | 2008-540678 A | 11/2008 |
| JP | 2012-501180 A | 1/2012 |
| WO | WO 92/08796 A1 | 5/1992 |
| WO | WO 94/28143 A1 | 12/1994 |
| WO | WO 2005/047458 A2 | 5/2005 |
| WO | WO 2006/008548 A2 | 1/2006 |
| WO | WO 2009/091826 A2 | 7/2009 |
| WO | WO 2010/104949 A2 | 9/2010 |
| WO | WO 2011/041093 A1 | 4/2011 |
| WO | WO 2012/031744 A1 | 3/2012 |
| WO | WO 2012/079000 A1 | 6/2012 |
| WO | WO 2012/163805 A1 | 12/2012 |
| WO | WO 2013/123061 A1 | 8/2013 |
| WO | WO 2013/154760 A1 | 10/2013 |

OTHER PUBLICATIONS

Ali et al., "Remissions of Multiple Myeloma during a First-in-Humans Clinical Trial of T Cells Expressing an Anti-B-Cell Maturation Antigen Chimeric Antigen Receptor," ASH 57th Annual Meeting & Exposition, Dec. 5-8, 2015.

Ali et al., "T cells expressing an anti-B-cell maturation antigen chimeric antigen receptor cause remissions of multiple myeloma," Blood, 128(13): 1688-1700 (Jul. 13, 2016).

Atanackovic et al., "CD4+CD25+FOXP3+ T regulatory cells reconstitute and accumulate in the bone marrow of patients with multiple myeloma following allogeneic stem cell transplantation", Haematologica, vol. 93, No. 3, pp. 423-430 (2008).

Autologous CD8+ T-cells Expressing an Anti-BCMA CAR in Patients With Myeloma, U.S. National Library of Medicine, accessed online at <clinicaltrials.gov/ct2/show/NCT03448978?term=descartes-08&draw=2&rank=2>, on Nov. 15, 2019, updated on Jun. 5, 2019.

Avery et al., "BAFF Selectively Enhances the Survival of Plasmablasts Generated from Human Memory B Cells", 112 Journal of Clinical Investigation 286-97 (2003).

Barber et al., "Treatment of multiple myeloma with adoptively transferred chimeric NKG2D receptor-expressing T cells," Gene Ther., 18 (5), 509-516 (2011) (author manuscript).

Bausch-Fluck et al., "A Mass Spectrometric-Derived Cell Surface Protein Atlas", PLOS One, vol. 10, No. 4, e0121314, pp. 1-22 (2015).

Bausch-Fluck et al., "The in silico human surfaceome", PNAS, vol. 115, No. 46, pp. E10988-10997 (2018).

Beatty et al., "Safety and antitumor activity of chimeric antigen receptor modified T cells in patients with chemotherapy refractory metastatic pancreatic cancer," abstract, 2015 ASCO Annual Meeting.

Beck et al., "Strategies and challenges for the next generation of therapeutic antibodies", Nature, vol. 10, pp. 345-352 (2010).

Bellucci et al., "Graft-versus-tumor response in patients with multiple myeloma is associated with antibody response to BCMA, a plasma-cell membrane receptor," Blood, 105 (10), 3945-3950 (2005).

Benjamin et al., "CD56 targeted chimeric antigen receptors for immunotherapy of multiple myeloma," Cancer Res., 72, Abstract 3499 (2012).

Biagi et al., "Chimeric T-cell Receptors—New Challenges for Targeted Immunotherapy in Hematologic Malignancies", 92 Haematologica 381-88 (2007).

Bird et al., "Single-chain antigen-binding proteins," Science, 242 (4877), 423-426 (1988).

Bleumer et al., "A phase II trial of chimeric monoclonal antibody G250 for advanced renal cell carcinoma patients", British Journal of Cancer, vol. 90, pp. 985-990 (2004).

Braendstrup et al., "The long road to the first FDA-approved gene therapy: chimeric antigen receptor T cells targeting CD19", Cytotherapy, vol. 22, pp. 57-69 (2020).

Brandtzaeg, "Function of mucosa-associated lymphoid tissue in antibody formation," Immunol. Invest., 39 (4-5), 303-355 (2010).

Braga et al., "The Role of Regulatory T Cells and TH17 Cells in Multiple Myeloma", Clinical and Developmental Immunology, vol. 2012, Article ID 293479, pp. 1-4 (2012).

Brash et al., "Strontium phosphate transfection of human cells in primary culture: stable expression of the simian virus 40 large-T-antigen gene in primary human bronchial epithelial cells," Mol. Cell Biol., 7 (5), 2031-2034 (1987).

Brenner et al., "Adoptive T cell therapy of cancer," Curr. Opin. Immunol., 22 (2), 251-257 (2010) (author manuscript).

Brentjens et al., "Eradication of systemic B-cell tumors by genetically targeted human T lymphocytes co-stimulated by CD80 and interleukin-15," Nat. Med., 9 (3), 279-286 (2003).

Brentjens et al., "Genetically targeted T cells eradicate systemic acute lymphoblastic leukemia xenografts," Clin. Cancer Res., 13 (18 Pt 1), 5426-5435 (2007).

Brentjens et al., "Treatment of Chronic Lymphocytic Leukemia With Genetically Targeted Autologous T Cells: Case Report of an Unforeseen Adverse Event in a Phase I Clinical Trial", Molecular Therapy, vol. 18, No. 4, pp. 666-668 (2010).

Brentjens et al., "Safety and persistence of adoptively transferred autologous CD19-targeted T cells in patients with relapsed or chemotherapy refractory B-cell leukemias," Blood, 118 (18), 4817-4828 (2011).

Brimnes et al., "Increased Level of both CD4+FOXP3+ Regulatory T Cells and CD14+HLA-DR-/low Myeloid-Derived Suppressor Cells and Decreased Level of Dendritic Cells in Patients with Multiple Myeloma", Scandinavian Journal of Immunology, vol. 72, pp. 540-547 (2010).

Bross et al., "Approval Summary: Gemtuzumab Ozogamicin in Relapsed Acute Myeloid Leukemia", 7 Clinical Cancer Research 1490-96 (2001).

Brown et al., "The Expression of T Cell Related Costimulatory Molecules in Multiple Myeloma," Leuk. Lymphoma, 31(3-4): 379-84 (1998).

Brudno et al., "T Cells Genetically Modified to Express an Anti-B-Cell Maturation Antigen Chimeric Antigen Receptor Cause Remissions of Poor-Prognosis Relapsed Multiple Myeloma," J. Clin. Oncol., 36(22): 2267-2280 (2018).

(56) References Cited

OTHER PUBLICATIONS

Bu et al., "Pre-clinical validation of B cell maturation antigen (BCMA) as a target for T cell immunotherapy of multiple myeloma," *Oncotarget*, 9(40): 25764-25780 (2018).

Caers et al., "Multiple Myeloma: an Update on Diagnosis and Treatment", 81 *European Journal of Haematology* 329-43 (2008).

Cameron et al., "Identification of a Titin-Derived HLA-A1-Presented Peptide as a Cross-Reactive Target for Engineered MAGE A3-Directed T Cells," *Science Translational Magazine*, 5(197): 197ra103 (2013).

Carpenter et al., B-cell Maturation Antigen Is a Promising Target for Genetically-Modified T-Cell Therapy of Multiple Myeloma, *Blood*, 120(21): 937-937 (2012).

Carpenito et al., "Control of Large, Established Tumor Xenografs with Generically Retargeted Human T Cells Containing CD28 and CD137 Domains", 106 *Proceedings of the National Academy of Sciences of USA* 3360-65 (2009).

Carpenter et al., "B-cell Maturation Antigen is a promising target for adoptive T-cell therapy of multiple myeloma," *Clin. Cancer Res.*, 19 (8), 2048-2060 (2013), with supplementary material.

Cartellieri et al., "Chimeric Antigen Receptor-Engineered T Cells for Immunotherapy of Cancer," *J. Biomedicine and Biotechnology*, 2010: 1-13 (2010).

Caruso et al., "Tuning sensitivity of CAR to EGFR density limits recognition of normal tissue while maintaining potent anti-tumor activity," *Cancer Res.*, 75(17): 3505-3518 (2015).

Case No. IPR2021-01484, U.S. Pat. No. 9,765,342: Notice of Filing Date Accorded to Petition and Time for Filing Patent Owner Preliminary Response, mailed on Sep. 16, 2021.

Case No. IPR2021-01484, U.S. Pat. No. 9,765,342: Declaration of Djordje Atanackovic, M.D., filed on Dec. 16, 2021.

Case No. IPR2021-01484, U.S. Pat. No. 9,765,342: Curriculum Vitae of Djordje Atanackovic, M.D., filed on Dec. 16, 2021.

Case No. IPR2021-01484, U.S. Pat. No. 9,765,342: Order—Conduct of the Proceeding 37 C.F.R. § 4Z5, mailed on Jan. 11, 2022.

Case No. IPR2021-01484, U.S. Pat. No. 9,765,342: Petitioner's Reply to Patent Owner's Preliminary Response, filed on Jan. 19, 2022.

Chauhan et al., "Human CD4(+) T-Cells: A Role for Low-Affinity Fc Receptors," *Front. Immunol.*,7: 215 (2016).

Cheadle et al., "Natural expression of the CD19 antigen impacts the long-term engraftment but not antitumor activity of CD19-specific engineered T cells," *J. Immunol.*, 184 (4), 1885-1896 (2010), with supplementary material.

Ch'En et al., "Characterisation of monoclonal antibodies to the TNF and TNF receptor families," *Cellular Immunology*, 236 (1-2): 78-85 (2005).

Chinnasamy et al., "Gene Therapy Using Genetically Modified Lymphocytes Targeting VEGFR-2 Inhibits the Growth of Vascularized Syngenic Tumors in Mice", 120 *Journal of Clinical Investigation* 3953-68 (2010).

Chiu et al., "Hodgkin lymphoma cells express TACI and BCMA receptors and generate survival and proliferation signals in response to BAFF and APRIL," *Blood*, 109 (2), 729-739 (2007).

Chmielewski et al., "T Cell Activation by Antibody-Like Immunoreceptors: Increase in Affinity of the Single-Chain Fragment Domain above Threshold Does Not Increase T Cell Activation against Antigen-Positive Target Cells but Decreases Selectivity," *J. Immunol.*, 173(12): 7647-7653 (2004).

Cho et al., "Targeting B Cell Maturation Antigen (BCMA) in Multiple Myeloma: Potential Uses of BCMA-Based Immunotherapy", 9 *Frontiers in Immunology*, Article 1821 (Aug. 2018).

Colbère-Garapin et al., "A new dominant hybrid selective marker for higher eukaryotic cells," *J. Mol. Biol.*, 150 (1), 1-14 (1981).

Conese et al., "Gene therapy progress and prospects: episomally maintained self-replicating systems," *Gene Ther.*, 11 (24), 1735-1742 (2004).

Cooper et al., "T-cell clones can be rendered specific for CD19: toward the selective augmentation of the graft-versus-B-lineage leukemia effect," *Blood*, 101 (4), 1637-1644 (2003).

Curriculum vitae of Dr. Abhinav Deol, filed in Petition for Inter Partes Review of U.S. Pat. No. 9,765,342, IPR2021-01484, filed Sep. 9, 2021.

Curriculum vitae of Dr. Ingrid Hsieh-Yee, filed in Petition for Inter Partes Review of U.S. Pat. No. 9,765,342, IPR2021-01484, filed Sep. 9, 2021.

Curriculum vitae of Dr. Hidde L. Ploegh, filed in Petition for Inter Partes Review of U.S. Pat. No. 9,765,342, IPR2021-01484, filed Sep. 9, 2021.

De Claro et al., "U.S. Food and Drug Administration Approval Summary: Brentuximab Vedotin for the Treatment of Relapsed Hodgkin Lymphoma or Relapsed Systemic Anaplastic Large-Cell Lymphoma", 18 *Clinical Cancer Research* 5845-5849 (2012).

Declaration of Dr. Abhinav Deol in Support of Petition for Inter Partes Review of U.S. Pat. No. 9,765,342 IPR2021-01484, filed Sep. 9, 2021.

Declaration of Dr. Ingrid Hsieh-Yee in Support of Petition for Inter Partes Review of U.S. Pat. No. 9,765,342 IPR2021-01484, filed Sep. 9, 2021.

Declaration of Dr. Hidde L. Ploegh in Support of Petition for Inter Partes Review of U.S. Pat. No. 9,765,342 IPR2021-01484, filed Sep. 9, 2021.

Demko et al., "FDA Drug Approval Summary: Alemtuzumab as a Single-Agent Treatment for B-Cell Chronic Lymphocytic Leukemia", 13 *The Oncologist* 167-74 (2008).

Di Bernardo et al., "Humoral immunotherapy of multiple myeloma: perspectives and perplexities", *Expert Opinion on Biological Therapy*, vol. 10, No. 6, pp. 863-873 (2010).

Di Stasi et al., "T Lymphocytes Coexpressing CCR4 and a Chimeric Antigen Receptor Targeting CD30 Have Improved Homing and Antitumor Activity in a Hodgkin Tumor Model", 113 *Blood* 6392-402 (2009).

Dimopoulos et al., "Multiple Myeloma", 21 *Annals of Oncology* vii143-viil 50 (2010).

Eshhar et al., "Specific activation and targeting of cytotoxic lymphocytes through chimeric single chains consisting of antibody-binding domains and the gamma or zeta subunits of the immunoglobulin and T-cell receptors," *Proc. Natl. Acad. Sci. USA*, 90 (2), 720-724 (1993).

Feyler et al., "$CD4^+CD25^+FoxP3^+$ regulatory T cells are increased whilst $CD3^+CD4-CD8-\alpha\beta TCR^+$ Double Negative T Cells are decreased in the peripheral blood of patients with multiple myeloma which correlates with disease burden", *British Journal of Haematology*, vol. 144, pp. 686-695 (2009).

File History for European Patent Application No. EP13714125, filed in Petition for Inter Partes Review of U.S. Pat. No. 9,765,342, IPR2021-01484, filed Sep. 9, 2021.

File History for U.S. Pat. No. 9,765,342, filed in Petition for Inter Partes Review of U.S. Pat. No. 9,765,342, IPR2021-01484, filed Sep. 9, 2021.

Finney et al., "Chimeric Receptors Providing Both Primary and Costimulatory Signaling in T Cells from a Single Gene Product", 161 *Journal of Immunology* 2791-97 (1998).

Finney et al., "Activation of Resisting Human Primary T Cells with Chimeric Receptors: Costimulation from CD28, Inducible Costimulator, CD134 and CD137 in Series with Signals from the TCRζ Chain", 172 *Journal of Immunology* 104-13 (2004).

Fuhrmann-Benzakein et al., "Inducible and irreversible control of gene expression using a single transgene," *Nuc. Acid. Res.*, 28 (23), E99 (2000).

Gattinoni et al., "Adoptive immunotherapy for cancer: building on success," *Nat. Rev. Immunol.*, 6 (5), 383-393 (2006).

Geffen et al., "New Drugs for the Treatment of Cancer, 1990-2001", 4 *Israel Medical Association Journal* 1124-31 (2002).

Gentile et al., "Emerging biological insights and novel treatment strategies in multiple myeloma", *Expert Opinion on Emerging Drugs*, vol. 17, No. 7, pp. 407-438 (2012).

(56) References Cited

OTHER PUBLICATIONS

Giannopoulos et al., "The frequency of T regulatory cells modulates the survival of multiple myeloma patients: detailed characterization of immune status in multiple myeloma", *British Journal of Cancer*, vol. 106, pp. 546-552 (2012).

Gross et al., "Expression of immunoglobulin-T-cell receptor chimeric molecules as functional receptors with antibody-type specificity," *Proc. Natl. Acad. Sci. USA*, 86 (24), 10024-10028 (1989).

Guest et al., "The Role of Extracellular Spacer Regions in the Optimal Design of Chimeric Immune Receptors: Evaluation of Four Different scFvs and Antigens," *J. Immunother.*, 28(3): 203-211 (2005).

Gupta et al., "Flow cytometric immunophenotyping and minimal residual disease analysis in multiple myeloma," *Am. J. Clin. Pathol.*, 132 (5), 728-732 (2009).

Hajela, "Structure and Function of Fc Receptors", *Biochemical Education*, vol. 19, No. 2, pp. 50-57 (1991).

Hammer, "CD19 as an Attractive Target for Antibody-Based Therapy", 4 *mAbs* 571-77 (2012).

Haynes et al., "Single-Chain Antigen Recognition Receptors that Costimulate Potent Rejection of Established Experimental Tumors", 100 *Blood* 3155-63 (2002).

Hermans et al., "The VITAL assay: a versatile fluorometric technique for assessing CTL- and NKT-mediated cytotoxicity against multiple targets in vitro and in vivo," *J. Immunol. Methods*, 285 (1), 25-40 (2004).

Holliger et al., "Engineered antibody fragments and the rise of single domains," *Nat. Biotechnol.*, 23 (9), 1126-1136 (2005).

Hombach et al., "An Anti-CD30 Chimeric Receptor That Mediates CD3-ζ-Independent T-Cell Activation Against Hodgkin's Lymphoma Cells in the presence of Soluble CD30", 58 *Cancer Research* 1116-19 (1998).

Hombach et al., "T Cell Activation by Antibody-Like Immunoreceptors: the Position of the Binding Epitope within the Target Molecule Determines the Efficiency of Activation of Redirected T Cells," *J. Immunol.*, 178(7): 4650-4657 (2007).

Huang et al., "Recent Advances in CAR-T Cell Engineering", 13 *Journal of Hematology and Oncology* (2020).

Hudecek et al., "Receptor Affinity and Extracellular Domain Modifications Affect Tumor Recognition by ROR1-Specific Chimeric Antigen Receptor T Cells," *Clin. Cancer Res.*, 19(12): 3153-3164 (2013).

Hudecek et al., "The Nonsignaling Extracellular Spacer Domain of Chimeric Antigen Receptors Is Decisive for In Vivo Antitumor Activity," *Cancer Immunol. Res.*, 3(2): 125-35 (2015).

Hughes et al., "Transfer of a TCR gene derived from a patient with a marked antitumor response conveys highly active T-cell effector functions," *Hum. Gene Ther.*, 16 (4), 457-472 (2005).

Huston et al., "Protein engineering of antibody binding sites: recovery of specific activity in an anti-digoxin single-chain Fv analogue produced in *Escherichia coli*," *Proc. Natl. Acad. Sci. USA*, 85 (16), 5879-5883 (1988).

Imai et al., "Chimeric Receptors with 4-1BB Signaling Capacity Provoke Potent Cytotoxicity Against Acute Lymphoblastic Leukemia", 18 *Leukemia* 676-84 (2004).

Imai et al., "Genetic modification of primary natural killer cells overcomes inhibitory signals and induces specific killing of leukemic cells," Blood, 106(1): 376-383 (2005).

Indra et al., "Temporally-controlled site-specific mutagenesis in the basal layer of the epidermis: comparison of the recombinase activity of the tamoxifen-inducible Cre-ER(T) and Cre-ER(T2) recombinases," *Nucleic Acids Res.*, 27 (22), 4324-4327 (1999).

Inter Partes Review Case No. IPR2021-01484, U.S. Pat. No. 9,765,342: Patent Owner's Mandatory Notices Pursuant to 37 C.F.R. § 42.8, filed on Sep. 30, 2021.

Inter Partes Review Case No. IPR2021-01484, U.S. Pat. No. 9,765,342: Patent Owner's Updated Mandatory Notices, filed on Dec. 16, 2021.

Inter Partes Review Case No. IPR2021-01484, U.S. Pat. No. 9,765,342: Patent Owner the United States of America's Preliminary Response, filed on Dec. 16, 2021.

Inter Partes Review Case No. IPR2021-01484, U.S. Pat. No. 9,765,342: Patent Owner Sur-Reply, filed on Feb. 2, 2022.

International Preliminary Report on Patentability, Application No. PCT/US2013/032029, dated Oct. 14, 2014.

International Search Report, Application No. PCT/US2013/032029, dated Oct. 17, 2013.

James et al., "Antigen Sensitivity of CD22-Specific Chimeric TCR Is Modulated by Target Epitope Distance from the Cell Membrane," *J. Immunol.*, 180(10): 7028-7038 (2008).

James et al., "Rituximab in Chronic Lymphocytic Leukemia", 28 *Advances in Therapy* 534-54 (2011).

Jena et al., "Redirecting T-cell specificity by introducing a tumor-specific chimeric antigen receptor," *Blood*, 116(7): 1035-1044 (2010).

Jensen et al., "Anti-transgene rejection responses contribute to attenuated persistence of adoptively transferred CD20/CD19-specific chimeric antigen receptor redirected T cells in humans," *Biol. Blood Marrow Transplant.*, 16 (9), 1245-1256 (2010) (author manuscript).

Johnston, "Biolistic transformation: microbes to mice," *Nature*, 346 (6286), 776-777 (1990).

June, "Adoptive T cell therapy for cancer in the clinic," *J. Clin. Invest.*, 117 (6), 1466-1476 (2007).

Kalled, "The role of BAFF in immune function and implications for autoimmunity," *Immunol. Rev.*, 204, 43-54 (2005).

Kalled Sequence Listing from WO 2010/104949 (Sep. 16, 2010).

Kalos et al., "T cells with chimeric antigen receptors have potent antitumor effects and can establish memory in patients with advanced leukemia," *Sci. Transl. Med.*, 3 (95), 95ra73 (2011).

Kay et al., "Blood levels of immune cells predict survival in myeloma patients: results of an Eastern Cooperative Oncology Group phase 3 trial for newly diagnosed multiple myeloma patients," *Blood*, 98(1): 23-28 (2001).

Kent et al., "Ouabain resistance conferred by expression of the cDNA for a murine $Na^+$, $K+$-ATPase alpha subunit," *Science*, 237, 901-903 (1987).

Kershaw et al., "Supernatural T cells: genetic modification of T cells for cancer therapy," *Nat. Rev. Immunol.*, 5 (12), 928-940 (2005).

Kochenderfer et al., "Construction and preclinical evaluation of an anti-CD19 chimeric antigen receptor," *J. Immunother.*, 32 (7), 689-702 (2009).

Kochenderfer et al., "A Phase I Clinical Trial of Treatment of B-Cell Malignancies with Autologous Anti-CD19-CAR-Transduced T Cells," *52nd Annual Meeting of the American-Society-of-Hematology*, 116 (Abstract 2865), 1179-1180 (2010).

Kochenderfer et al., "Eradication of B-lineage cells and regression of lymphoma in a patient treated with autologous T-cells genetically enginered to recognize CD19," *Blood*, 116 (20), 4099-4102 (2010).

Kochenderfer et al., "Adoptive transfer of syngeneic T cells transduced with a chimeric antigen receptor that recognizes murine CD19 can eradicate lymphoma and normal B cells," *Blood*, 116 (19), 3875-3886 (2010).

Kochenderfer & Rosenberg, "Letter to the Editor", and Kalos et al., "Authors' Reply, Chimeric Antigen Receptor-Modified T Cells in CLL", 365 *New England Journal of Medicine* 1937-39 (2011).

Kochenderfer et al., "B-cell depletion and remissions of malignancy along with cytokine-associated toxicity in a clinical trial of anti-CD19 chimeric-antigen-receptor-transduced T cells," *Blood*, 119 (12), 2709-2720 (2012) (originally published online Dec. 8, 2011).

Kramer et al., "Transgene control engineering in mammalian cells," *Methods Mol. Biol.*, 308, 123-143 (2005).

Krenciute et al., "Characterization and Functional Analysis of scFv-based Chimeric Antigen Receptors to Redirect T Cells to IL13Rα2-positive Glioma," *Mol. Ther.*, 24(2): 354-363 (2016).

Kumar et al., "Improved Survival in Multiple Myeloma and the Impact of Novel Therapies", 111 *Blood* 2516-20 (2008).

Laabi et al., "A new gene, BCM, on chromosome 16 is fused to the interleukin 2 gene by a t(4;16)(g26;p13) translocation in a malignant T cell lymphoma," *EMBO J.*, 11 (11), 3897-3904 (1992).

(56) References Cited

OTHER PUBLICATIONS

Laabi et al., "The BCMA gene, preferentially expressed during B lymphoid maturation, is bidirectionally transcribed," Nucleic Acids Res., 22 (7), 1147-1154 (1994).
Lamers et al., "Treatment of Metastatic Renal Cell Carcinoma With Autologous T-Lymphocytes Genetically Retargeted Against Carbonic Anhydrase IX: First Clinical Experience," J. Clin. Oncol., 24(13): e20-2 (2006).
Lamers et al., "Treatment of Metastatic Renal Cell Carcinoma With CAIX CAR-engineered T cells: Clinical Evaluation and Management of On-target Toxicity," Mol. Ther., 21(4): 904-912 (2013).
Lanitis et al., "Redirected Antitumor Activity of Primary Human Lymphocytes Transduced with a Fully Human Anti-mesothelin Chimeric Receptor", 20 Molecular Therapy 633-43 (2012).
Latza et al., "The human OX40 homolog: cDNA structure, expression and chromosomal assignment of the ACT35 antigen," Eur. J. Immunol., 24 (3), 677-683 (1994).
Lenhoff et al., "Impact on survival of high-dose therapy with autologous stem cell support in patients younger than 60 years with newly diagnosed multiple myeloma: a population-based study," Blood, 95(1): 7-11 (2000).
Levine, "Molecular Mechanisms of Soluble Cytokine Receptor Generation," J. of Biological Chemistry, 283(21): 14177-14181 (2008).
Lin et al., "Flow cytometric immunophenotypic analysis of 306 cases of multiple myeloma," Am. J. Clin. Pathol., 121 (4), 482-488 (2004).
Liu et al., "Adoptive T-cell therapy of B-cell malignancies: conventional and physiological chimeric antigen receptors," Cancer Lett., 316 (1), 1-5 (2012).
Liu et al., "Affinity-tuned ErbB2 or EGFR chimeric antigen receptor T cells exhibit an increased therapeutic index against tumors in mice," Cancer Res., 75(17): 3596-3607 (2015).
Lo et al., "Anti-GD3 Chimeric sFv-CD28/T-Cell Receptor ζ Designer T Cells for Treatment of Metastatic Melanoma and Other Neuroectodermal Tumors", 16 Clinical Cancer Research 2769-80 (2010).
Lonial et al., "Treatment options for relapsed and refractory multiple myeloma, " Clin. Cancer Res., 17 (6), 1264-1277 (2011).
Long et al., "4-1BB Costimulation Ameliorates T Cell Exhaustion Induced by Tonic Signaling of Chimeric Antigen Receptors," Nat. Med., 21(6): 581-590 (2015).
Lowy et al., "Isolation of transforming DNA: cloning the hamster aprt gene," Cell, 22 (3), 817-823 (1980).
Mackay et al., "BAFF and APRIL: a tutorial on B cell survival," Annu. Rev. Immunol., 21, 231-264 (2003).
Mahindra et al., "Latest advances and current challenges in the treatment of multiple myeloma", Nature, vol. 9, pp. 135-143 (2012).
Mannering et al., "A sensitive method for detecting proliferation of rare autoantigen-specific human T cells," J. Immunol. Methods, 283 (1-2), 173-183 (2003).
Maus et al., "T Cells Expressing Chimeric Antigen Receptors Can Cause Anaphylaxis in Humans," Can. Immunol. Res., 1(1): 26-31 (2013).
Miller et al, "Successful adoptive transfer and in vivo expansion of human haploidentical NK cells in patients with cancer," Blood, 105(8): 3051-3057 (2005).
Milone et al., "Chimeric Receptors Containing CD137 Signal Transduction Domains Mediate Enhanced Survival of T-Cells and Increased Antileukemic Efficacy In Vivo", 17 Molecular Therapy 1453-64 (2009).
Mitsiades et al., "Future Directions of Next-Generation Novel Therapies, Combination Approaches, and the Development of Personalized Medicine in Myeloma", Journal of Clinical Oncology, vol. 29, No. 14, pp. 1916-1923 (2011).
Moreaux et al., "BAFF and APRIL protect myeloma cells from apoptosis induced by interleukin 6 deprivation and dexamethasone," Blood, 103 (8), 3148-3157 (2004).

Morgan et al., "Cancer regression in patients after transfer of genetically engineered lymphocytes," Science, 314 (5796), 126-129 (2006).
Morgan et al., "Case Report of a Serious Adverse Event Following the Administration of T Cells Transduced With a Chimeric Antigen Receptor Recognizing ErbB2," Mol. Ther., 18(4): 843-851 (2010).
Morgan, "Future drug developments in multiple myeloma: an overview of novel lenalidomide-based combination therapies", Blood Reviews, vol. 24, Suppl. 1, pp. S27-S32 (2010).
Mulligan et al., "Selection for animal cells that express the Escherichia coli gene coding for xanthine-guanine phosphoribosyltransferase," Proc. Natl. Acad. Sci. USA, 78 (4), 2072-2076 (1981).
Neelapu et al., "Axicabtagene Ciloleucel CAR T-Cell Therapy in Refractory Large B-Cell Lymphoma," N. Engl. J. Med., 377(26): 2531-2544 (2017).
Neri et al., "Neutralizing B-cell activating factor antibody improves survival and inhibits osteoclastogenesis in a severe combined immunodeficient human multiple myeloma model," Clin. Cancer Res., 13 (19), 5903-5909 (2007).
Nicholson et al., "Construction and Characterisation of a Functional CD19 Specific Single Chain Fv Fragment for Immunotherapy of B Lineage Leukaemia and Lymphoma", 34 Molecular Immunology 1157-65 (1997).
Ng et al., "B cell-activating factor belonging to the TNF family (BAFF)-R is the principal BAFF receptor facilitating BAFF costimulation of circulating T and B cells," J. Immunol., 173 (2), 807-817 (2004).
No et al., "Ecdysone-inducible gene expression in mammalian cells and transgenic mice," Proc. Natl. Acad. Sci., 93 (8), 3346-3351 (1996).
Novak et al., "Expression of BCMA, TACI, and BAFF-R in multiple myeloma: a mechanism for growth and survival," Blood, 103 (2), 689-694 (2004).
O'Connor et al., "BCMA is essential for the survival of long-lived bone marrow plasma cells," J. Exp. Med., 199 (1), 91-98 (2004).
O'Hare et al., "Transformation of mouse fibroblasts to methotrexate resistance by a recombinant plasmid expressing a prokaryotic dihydrofolate reductase," Proc. Natl. Acad. Sci. USA, 78 (3), 1527-1531 (1981).
Oken et al., "Prophylactic Antibiotics for the Prevention of Early Infection in Multiple Myeloma," Am. J. Med., 100(6): 624-628 (1996).
Osbourn et al., "Directed selection of MIP-1 alpha neutralizing CCR5 antibodies from a phage display human antibody library," Nat. Biotechnol., 16 (8), 778-781 (1998).
Palumbo et al., "Multiple myeloma," N. Engl. J. Med., 364 (11), 1046-1060 (2011).
Park et al., "Adoptive immunotherapy for B-cell malignancies with autologous chimeric antigen receptor modified tumor targeted T cells," Discov. Med., 9 (47), 277-288 (2010).
Payandeh et al., "The Applications of Anti-CD20 Antibodies to Treat Various B Cells Disorders", 109 Biomedicine & Pharmacotherapy 2415-26 (2019).
Pegram et al., "Tumor-targeted T cells modified to secrete IL-12 eradicate systemic tumors without need for prior conditioning", Blood, vol. 119, No. 18, pp. 4133-4141 (2012).
Petition for Inter Partes Review of U.S. Pat. No. 9,765,342 IPR2021-01484, filed Sep. 9, 2021.
Pizzolo et al., "CD30 Molecule (Ki-1 Ag): More than Just a Marker of CD30+ Lymphoma", 80 Haematologica 357-66 (1995).
Polonelli et al., "Antibody Complementarity-Determining Regions (CDRs) Can Display Differential Antimicrobial, Antiviral and Antitumor Activities", PLOS One, vol. 3, Issue. 6, e2371, pp. 1-9 (2008).
Pont et al., "γ-Secretase inhibition increases efficacy of BCMA-specific chimeric antigen receptor T cells in multiple myeloma," Blood, 134(19): 1585-1597 (2019).
Porter et al., "Chimeric antigen receptor-modified T cells in chronic lymphoid leukemia," N. Engl. J. Med., 365 (8), 725-733 (2011).
Preithner et al., "High Concentration of Therapeutic IgG1 Antibodies are Needed to Compensate for Inhibitions of Antibody-Dependent Cellular Cytotoxicity by Excess Endogenous Immunoglobulin G", 43 Molecular Immunology 1183-93 (2006).

(56) References Cited

OTHER PUBLICATIONS

"Prescribing Label for KYMRIAH® (tisagenlecleucel)", 24 pages (2017).
Pule et al., "Virus-specific T cells engineered to coexpress tumor-specific receptors: persistence and antitumor activity in individuals with neuroblastoma," *Nat. Med.*, 14 (11), 1264-1270 (2008).
Raab et al., "Multiple myeloma," *Lancet*, 374 (9686), 324-329 (2009).
Raje et al., "Anti-BCMA CAR T-Cell Therapy bb2121 in Relapsed or Refractory Multiple Myeloma," *N. Engl. J. Med.*, 380(18): 1726-1737 (2019).
Rajkumar, "Multiple Myeloma", 33 *Current Problems in Cancer* 7-64 (2009).
Rajkumar, "Treatment of multiple myeloma," *Nat. Rev. Clin. Oncol.*, 8 (8), 479-491 (2011).
Ramos et al., "Chimeric Antigen Receptor (CAR)-Engineered Lymphocytes for Cancer Therapy", 11 *Expert Opinion in Biological Therapy* 855-73 (2011).
Rapoport et al., "Combination immunotherapy using adoptive T-cell transfer and tumor antigen vaccination on the basis of hTERT and survivin after ASCT for myeloma," *Blood*, 117 (3), 788-797 (2011).
"Results of treatment of a myeloma patient with anti-BCMA CAR T-cells in clinical trial NCT03448978," unpublished as of Nov. 14, 2019.
Richardson et al., "Monoclonal antibodies in the treatment of multiple myeloma," *Br. J. Haematol.*, 154 (6), 745-754 (2011).
Rosenberg et al., "Adoptive cell transfer: a clinical path to effective cancer immunotherapy," *Nat. Rev. Cancer*, 8 (4), 299-308 (2008).
Rosenberg et al., "Personalized Cell Transfer Immunotherapy for B-Cell Malignancies and Solid Cancers", 19 *Molecular Therapy* 1928-30 (2011).
Rubio et al., "Ex vivo identification, isolation and analysis of tumor-cytolytic T cells," *Nat. Med.*, 9 (11), 1377-1382 (2003).
Rudikoff et al., "Single amino acid substitution altering antigen-binding specificity," *Proc. Natl. Acad. Sci. USA*, 79:1979-1983 (Mar. 1982).
Russian Patent Office, English translation of Office Action issued in Russian Patent Application No. 2014144143, 4 Pages, dated Jul. 10, 2017.
Ryan et al., "Antibody targeting of B-cell maturation antigen on malignant plasma cells," *Mol. Cancer Ther.*, 6 (11), 3009-3018 (2007).
Sadelain et al., "The promise and potential pitfalls of chimeric antigen receptors," *Curr. Opin. Immunol.*, 21 (2), 215-223 (2009).
Saini et al., "Beyond trastuzumab: Ner treatment options for HER2-positive breast cancer", *The Breast*, vol. 20, S3, pp. S20-S27 (2011).
Salit et al., "Reduced-intensity allogeneic hematopoietic stem cell transplantation for multiple myeloma: a concise review," *Clin. Lymphoma Myeloma Leuk.*, 11 (3), 247-252 (2011).
Sanchez et al., "Serum B-cell maturation antigen is elevated in multiple myeloma and correlates with disease status and survival," *British J. of Haematology*, 158: 727-738 (2012).
Santerre et al., "Expression of prokaryotic genes for hygromycin B and G418 resistance as dominant-selection markers in mouse L cells," *Gene*, 30 (1-3), 147-156 (1984).
Savage et al., "Biphasic Pattern of Bacterial Infection in Multiple Myeloma," *Ann. Intern. Med.*, 96(1): 47-50 (1982).
Savoldo et al., "CD28 costimulation improves expansion and persistence of chimeric antigen receptor-modified T cells in lymphoma patients," *J. Clin. Invest.*, 121 (5), 1822-1826 (2011).
Schiemann et al., "An essential role for BAFF in the normal development of B cells through a BCMA-independent pathway," *Science*, 293 (5537), 2111-2114 (2001).
Scott et al., "Antibody therapy of cancer", *Nature*, vol. 12, pp. 278-287 (2012).
Shirasu et al., "Construction and Molecular Characterization of Human Chimeric T-Cell Antigen Receptors Specific for Carcinoembryonic Antigen", 30 *Anticancer Research* 2731-38 (2010).
Singer et al., "Genes and Genomes," vol. 1, moscow "MIR," p. 35 (1998).
Sommermeyer et al., "Chimeric antigen receptor-modified T cells derived from defined $CD8^+$ and $CD4^+$ subsets confer superior antitumor reactivity in vivo," *Leukemia*, 30(2): 492-500 (2016).
Song et al., "A fully human chimeric antigen receptor with potent activity against cancer cells but reduced risk for off-tumor toxicity," *Oncotarget*, 6(25): 21533-21546 (2015).
Soutar, "Distribution of plasma cells and other cells containing immunoglobulin in the respiratory tract of normal man and class of immunoglobulin contained therein," *Thorax*, 31 (2), 158-166 (1976).
Sun et al., "T Cells Expressing Constitutively Active Ad Resist Multiple Tumor-associated Inhibitory Mechanisms," *Mol. Ther.*, 18(11): 2006-2017 (2010).
Szoka et al., "Comparative properties and methods of preparation of lipid vesicles (liposomes)," *Annu. Rev. Biophys. Bioeng.*, 9, 467-508 (1980).
Szybalska et al., "Genetics of human cell line. IV. DNA-mediated heritable transformation of a biochemical trait," *Proc. Natl. Acad. Sci. USA*, 48, 2026-2034 (1962).
Tai et al., "Targeting B-cell maturation antigen in multiple myeloma," *Immunotherapy*, 7(11): 1187-1199 (2015).
Terakura et al., "Generation of CD19-chimeric antigen receptor modified CD8+ T cells derived from virus-specific central memory T cells," *Blood*, 119(1): 72-82 (2012).
Thistlethwaite et al., "Engineering T-Cells with Antibody-Based Chimeric Receptors for Effective Cancer Therapy", 7 *Current Opinion in Molecular Therapeutics* 48-55 (2005).
Thompson et al., "BAFF binds to the tumor necrosis factor receptor-like molecule B cell maturation antigen and is important for maintaining the peripheral B cell population," *J. Exp. Med.*, 192 (1), 129-135 (2000).
Till et al., "CD20-specific Adoptive Immunotherapy for Lymphoma Using a Chimeric Antigen Receptor with Both CD28 and 4-1BB Domains: Pilot Clinical Trial Results", 119 *Blood* 3940-50 (2012).
Turatti et al., "Redirected Activity of Human Antitumor Chimeric Immune Receptors is Governed by Antigen and Receptor Expression Levels and Affinity of Interaction," *J. Immunother.*, 30(7): 684-693 (2007).
Van De Donk et al., "Monoclonal antibody-based therapy as a new treatment strategy in multiple myeloma", *Leukemia*, vol. 26, pp. 199-213 (2012).
Van Der Veer et al., "The therapeutic human CD38 antibody daratumumab improves the anti-myeloma effect of newly emerging multi-drug therapies," *Blood Cancer J.*, 1(10): e41 (2011).
Vera et al., "T Lymphocytes Redirected Against the k Light Chain of Human Immunoglobulin Efficiently Kill Mature B Lymphocyte-Derived Malignant Cells", 108 *Blood* 3890-97 (2006).
Wadwa et al., "Receptor mediated glycotargeting," *J. Drug Target.*, 3 (2), 111-127 (1995).
Warzocha et al., "Plasma levels of tumour necrosis factor and its soluble receptors correlate with clinical features and outcome of Hodgkin's disease patients," *Brit. J. of Cancer*, 77(12): 2357-2362 (1998).
Westwood et al., "Adoptive Transfer of T Cells Modified with a Humanized Chimeric Receptor Gene Inhibits Growth of Lewis-Y-Expressing Tumors in Mice", 102 *Proceedings of National Academy of Sciences of USA*, 19051-56 (2005).
Wigler et al., "Transfer of purified herpes virus thymidine kinase gene to cultured mouse cells," *Cell*, 11 (1), 223-232 (1977).
Wigler et al., "Transformation of mammalian cells with an amplifiable dominant-acting gene," *Proc. Natl. Acad. Sci. USA*, 77 (6), 3567-3570 (1980).
Wilkie et al., "Retargeting of Human T Cells to Tumor-Associated MUC1: the Evolution of a Chimeric Antigen Receptor," *J. Immunol.*, 180(7): 4901-4909 (2008).
Woof et al., "Human antibody-Fc receptor interactions illuminated by crystal structures," *Nat. Rev. Immunol.*, 4 (2), 89-99 (2004).
Written Opinion of the International Searching Authority, Application No. PCT/US2013/032029, dated Oct. 11, 2014.
Xu et al., "B-cell maturation protein, which binds the tumor necrosis factor family members BAFF and APRIL, is dispensable for humoral immune responses," *Mol. Cell. Biol.*, 21 (12), 4067-4074 (2001).

(56) References Cited

OTHER PUBLICATIONS

Yang et al., "A simplified method for the clinical-scale generation of central memory-like CD8+ T cells after transduction with lentiviral vectors encoding antitumor antigen T-cell receptors," *J. Immunother.*, 33 (6), 648-658 (2010).
Yi, "Novel immunotherapies," *Cancer J.*, 15 (6), 502-510 (2009) (author manuscript).
Zhao et al., "A herceptin-based chimeric antigen receptor with modified signaling domains leads to enhanced survival of transduced T lymphocytes and antitumor activity," *J. Immunology*, 183 (9), 5563-5574 (2009), with supplementary material.
Zhang et al., "Engineering CAR-T Cells", 5 *Biomarker Research* (2017).
Zhong et al., "Chimeric Antigen Receptors Combining 4-1BB and CD28 Signaling Domains Augment PI$_3$kinase/AKT/Bcl-X$_L$ Activation and CD8$^+$ T Cell-Mediated Tumor Eradication", 18 *Molecular Therapy* 413-20 (2010).
U.S. Appl. No. 17/117,335, filed Dec. 10, 2020, Patented.
Almagro et al., "Humanization of antibodies", *Frontiers in Bioscience*, 13:1619-1633 (2008).
U.S. Appl. No. 14/389,677, filed Sep. 30, 2014, Patented.
U.S. Appl. No. 15/692,473, filed Aug. 31, 2017, Patented.
U.S. Appl. No. 16/683,417, filed Nov. 14, 2019, Patented.
U.S. Appl. No. 16/683,435, filed Nov. 14, 2019, Patented.
U.S. Appl. No. 16/683,453, filed Nov. 14, 2019, Patented.
U.S. Appl. No. 16/683,477, filed Nov. 14, 2019, Patented.
U.S. Appl. No. 16/683,494, filed Nov. 14, 2019, Patented.
U.S. Appl. No. 16/683,524, filed Nov. 14, 2019, Patented.
U.S. Appl. No. 16/683,543, filed Nov. 14, 2019, Patented.
U.S. Appl. No. 16/683,625, filed Nov. 14, 2019, Patented.
U.S. Appl. No. 16/684,962, filed Nov. 15, 2019, Patented.
U.S. Appl. No. 16/684,978, filed Nov. 15, 2019, Patented.
U.S. Appl. No. 16/684,994, filed Nov. 15, 2019, Patented.
U.S. Appl. No. 17/117,311, filed Dec. 10, 2020, Patented.
U.S. Appl. No. 17/117,335, filed Dec. 10, 2010, Patented.
U.S. Appl. No. 17/117,368, filed Dec. 10, 2020, Patented.
U.S. Appl. No. 17/745,067, filed May 16, 2022, Pending.
U.S. Appl. No. 17/938,529, filed Oct. 6, 2022, Pending.

\* cited by examiner

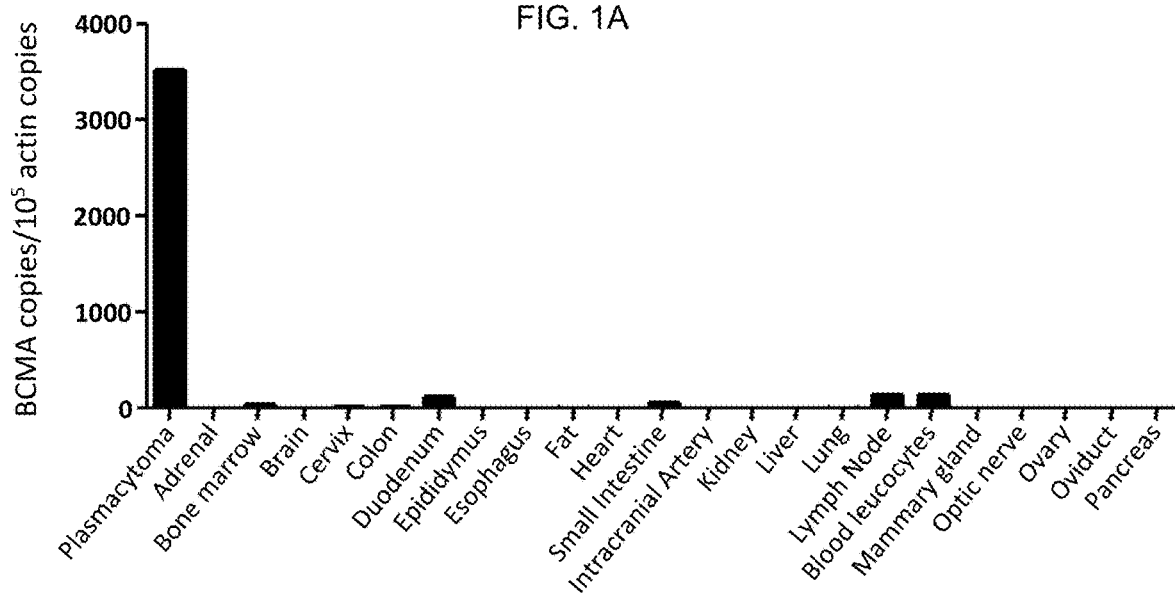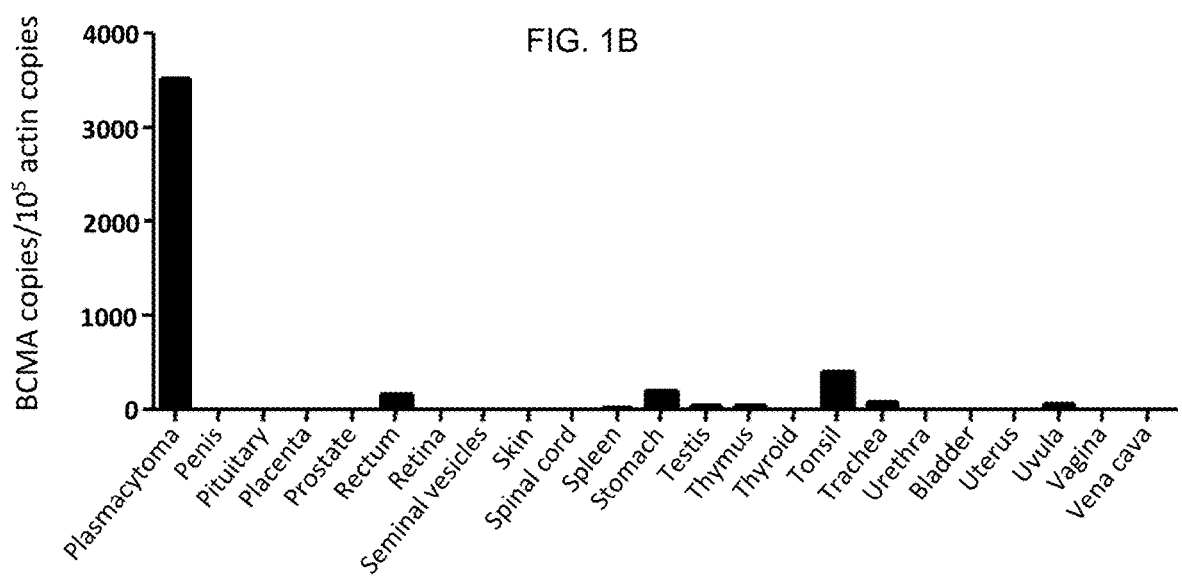

Fluorescence Intensity →

Fluorescence Intensity →

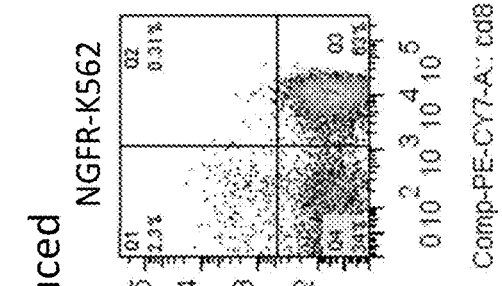
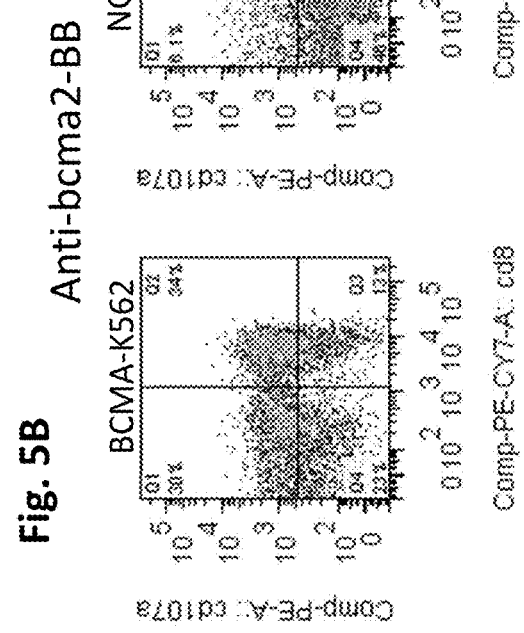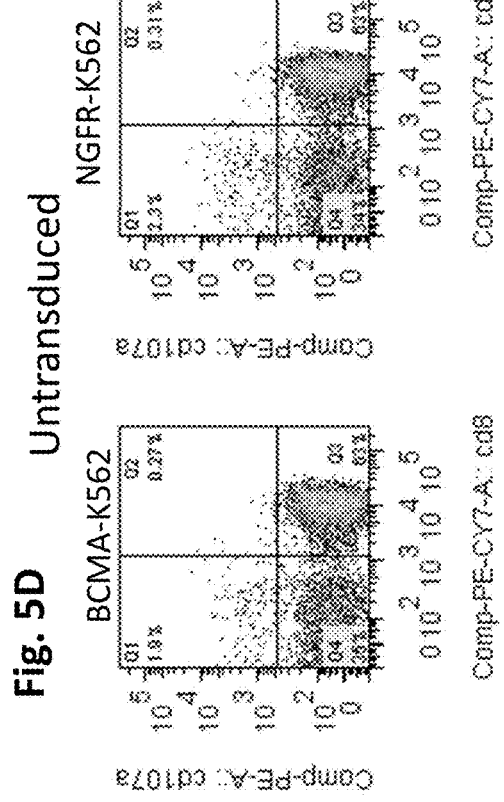
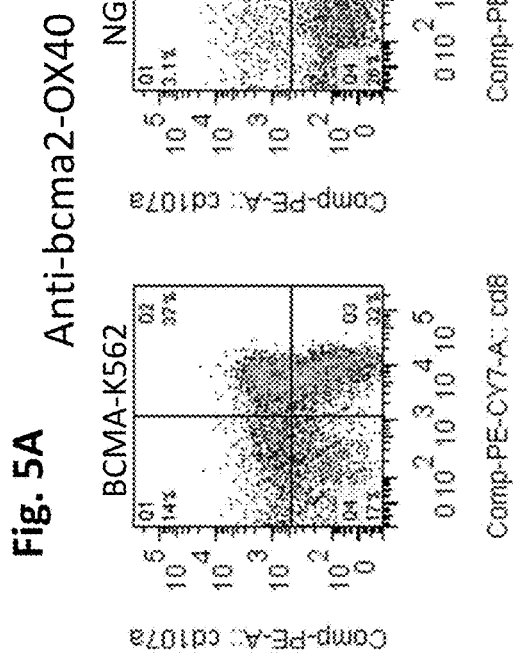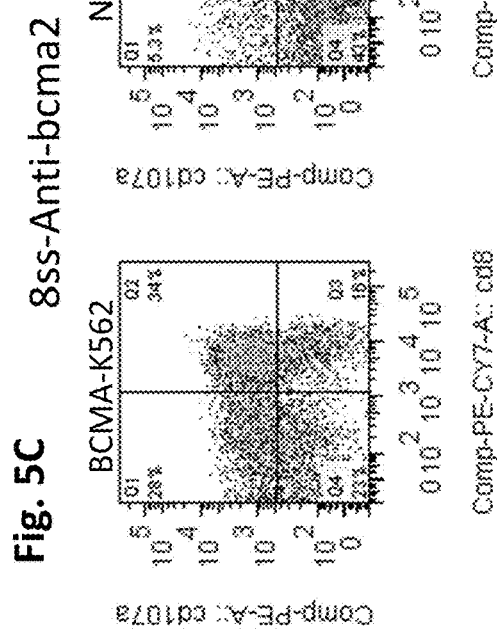
Fig. 5A  Anti-bcma2-OX40
Fig. 5B  Anti-bcma2-BB
Fig. 5C  8ss-Anti-bcma2
Fig. 5D  Untransduced

Fig. 6A
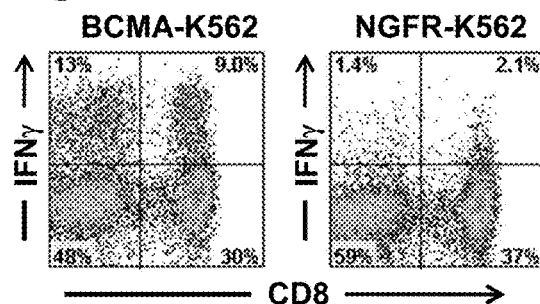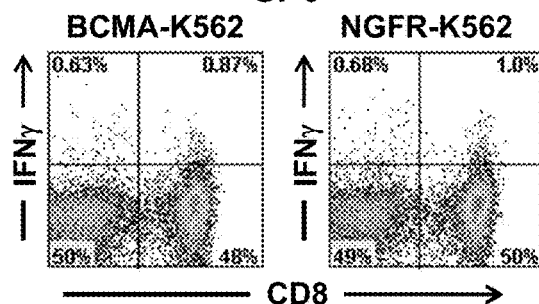
Fig. 6B
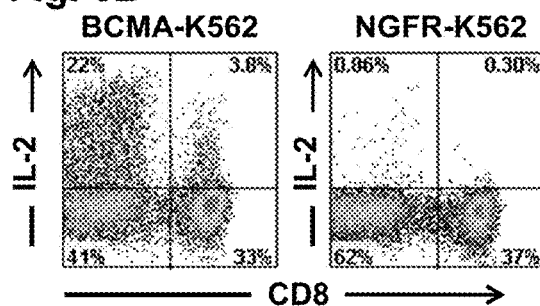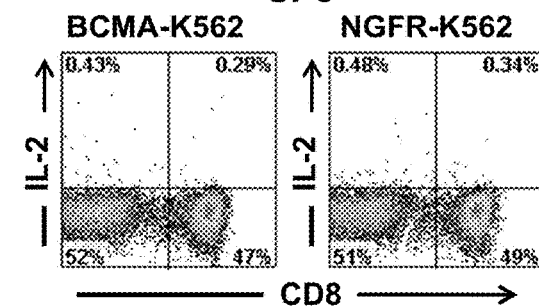
Fig. 6C
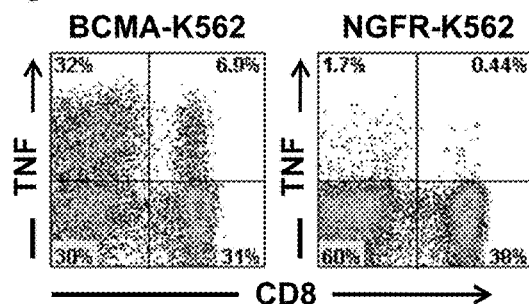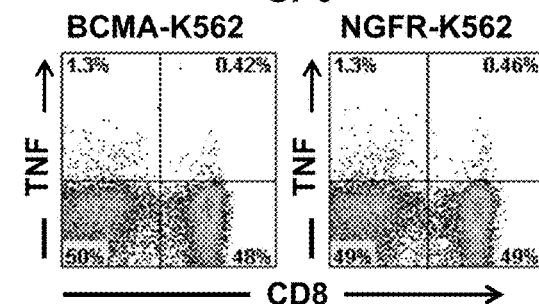

CHIMERIC ANTIGEN RECEPTORS TARGETING B-CELL MATURATION ANTIGEN

CROSS-REFERENCE TO RELATED APPLICATIONS

This patent application is a continuation of U.S. application Ser. No. 17/745,067, filed May 16, 2022, which is a continuation of U.S. application Ser. No. 17/117,368, filed Dec. 10, 2020, now U.S. Pat. No. 11,359,204, which is a continuation of U.S. application Ser. No. 16/683,524, filed Nov. 14, 2019, now U.S. Pat. No. 10,900,042, which is a continuation of U.S. application Ser. No. 15/692,473, filed Aug. 31, 2017, now U.S. Pat. No. 10,767,184, which is a continuation of U.S. application Ser. No. 14/389,677, filed Sep. 30, 2014, now U.S. Pat. No. 9,765,342, which is the U.S. National Phase of International Patent Application No. PCT/US2013/032029, filed Mar. 15, 2013, which claims the benefit of U.S. Provisional Patent Application No. 61/622,600, filed Apr. 11, 2012, each of which is incorporated by reference in its entirety herein.

STATEMENT REGARDING FEDERALLY SPONSORED RESEARCH AND DEVELOPMENT

This invention was made with Government support under project number ZIABC011417 by the National Institutes of Health, National Cancer Institute. The Government has certain rights in the invention.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 24,306 Byte XML file named "764892.XML," dated Oct. 6, 2022.

BACKGROUND OF THE INVENTION

Multiple myeloma (MM) is a malignancy characterized by an accumulation of clonal plasma cells (see, e.g., Palumbo et al., *New England J. Med.*, 364(11): 1046-1060 (2011), and Lonial et al., *Clinical Cancer Res.*, 17(6): 1264-1277 (2011)). Current therapies for MM often cause remissions, but nearly all patients eventually relapse and die (see, e.g., Lonial et al., supra, and Rajkumar, *Nature Rev. Clinical Oncol.*, 8(8): 479-491 (2011)). Allogeneic hematopoietic stem cell transplantation has been shown to induce immune-mediated elimination of myeloma cells; however, the toxicity of this approach is high, and few patients are cured (see, e.g., Lonial et al., supra, and Salit et al., *Clin. Lymphoma, Myeloma, and Leukemia*, 11(3): 247-252 (2011)). Currently, there are no clinically effective, FDA-approved monoclonal antibody or autologous T-cell therapies for MM (see, e.g., Richardson et al., *British J. Haematology*, 154(6): 745-754 (2011), and Yi, *Cancer Journal*, 15(6): 502-510 (2009)).

Adoptive transfer of T-cells genetically modified to recognize malignancy-associated antigens is showing promise as a new approach to treating cancer (see, e.g., Morgan et al., *Science*, 314(5796): 126-129 (2006); Brenner et al., *Current Opinion in Immunology*, 22(2): 251-257 (2010); Rosenberg et al., *Nature Reviews Cancer*, 8(4): 299-308 (2008), Kershaw et al., *Nature Reviews Immunology*, 5(12): 928-940 (2005); and Pule et al., *Nature Medicine*, 14(11): 1264-1270 (2008)). T-cells can be genetically modified to express chimeric antigen receptors (CARs), which are fusion proteins comprised of an antigen recognition moiety and T-cell activation domains (see, e.g., Kershaw et al., supra, Eshhar et al., *Proc. Natl. Acad. Sci. USA*, 90(2): 720-724 (1993), and Sadelain et al., *Curr. Opin. Immunol.*, 21(2): 215-223 (2009)).

For B-cell lineage malignancies, extensive progress has been made in developing adoptive T-cell approaches that utilize anti-CD19 CARs (see, e.g., Jensen et al., *Biology of Blood and Marrow Transplantation*, 16: 1245-1256 (2010); Kochenderfer et al., *Blood*, 116(20): 4099-4102 (2010); Porter et al., *The New England Journal of Medicine*, 365(8): 725-733 (2011); Savoldo et al., *Journal of Clinical Investigation*, 121(5): 1822-1826 (2011), Cooper et al., *Blood*, 101(4): 1637-1644 (2003); Brentjens et al., *Nature Medicine*, 9(3): 279-286 (2003); and Kalos et al., *Science Translational Medicine*, 3(95): 95ra73 (2011)). Adoptively transferred anti-CD19-CAR-transduced T-cells have cured leukemia and lymphoma in mice (see, e.g., Cheadle et al., *Journal of Immunology*, 184(4): 1885-1896 (2010); Brentjens et al., *Clinical Cancer Research*, 13(18 Pt 1): 5426-5435 (2007); and Kochenderfer et al., *Blood*, 116(19): 3875-3886 (2010)). In early clinical trials, adoptively transferred T-cells transduced with anti-CD19 CARs eradicated normal and malignant B-cells in patients with leukemia and lymphoma (see, e.g., Kochenderfer et 1., *Blood*, 116(20): 4099-4102 (2010); Porter et al., supra, Brentjens et al., *Blood*, 118(18): 4817-4828 (2011); and Kochenderfer et al., *Blood*, Dec. 8, 2011 (epublication ahead of print (2012)). CD19, however, is only rarely expressed on the malignant plasma cells of multiple myeloma (see, e.g., Gupta et al., *Amer. J. Clin. Pathology*, 132(5): 728-732 (2009); and Lin et al., *Amer. J. Clin. Pathology*, 121(4): 482-488 (2004)).

Thus, there remains a need for compositions that can be used in methods to treat multiple myeloma. This invention provides such compositions and methods.

BRIEF SUMMARY OF THE INVENTION

The invention provides an isolated or purified nucleic acid sequence encoding a chimeric antigen receptor (CAR), wherein the CAR comprises an antigen recognition moiety and a T-cell activation moiety, and wherein the antigen recognition moiety is directed against B-cell Maturation Antigen (BCMA).

BRIEF DESCRIPTION OF THE SEVERAL VIEWS OF THE DRAWING(S)

FIGS. 1A and 1B are graphs which depict experimental data illustrating the expression pattern of BCMA across a variety of human cell types, as determined using quantitative PCR. The results are expressed as the number of BCMA cDNA copies per $10^5$ actin cDNA copies.

FIGS. 2A-2L are graphs which depict experimental data illustrating that cell-surface BCMA expression was detected on multiple myeloma cell lines, but not on other types of cells, as described in Example 1. For all plots, the solid line represents staining with anti-BCMA antibodies, and the dashed line represents staining with isotype-matched control antibodies. All plots were gated on live cells.

FIG. 3A is a diagram which depicts a nucleic acid construct encoding an anti-BCMA CAR. From the N-terminus to the C-terminus, the anti-BCMA CAR includes an anti-BCMA scFv, the hinge and transmembrane regions of the CD8a molecule, the cytoplasmic portion of the CD28 molecule, and the cytoplasmic portion of the CD3ζ molecule.

FIGS. 3B-3D are graphs which depict experimental data illustrating that the anti-bcma1 CAR, the anti-bcma2 CAR, and the SP6 CAR (described in Example 2) are expressed on the surface of T-cells. Minimal anti-Fab staining occurred on untransduced (UT) cells. The plots are gated on $CD3^+$ lymphocytes. The numbers on the plots are the percentages of cells in each quadrant.

FIGS. 4A-4C are graphs which depict experimental data illustrating that T-cells expressing anti-BCMA CARs degranulate T-cells in a BCMA-specific manner, as described Example 3. The plots are gated on live CD3+ lymphocytes. The numbers on the plots are the percentages of cells in each quadrant.

FIGS. 5A-5D are graphs which depict experimental data illustrating that T-cells expressing anti-BCMA CARs degranulate T-cells in a BCMA-specific manner, as described Example 3. The plots are gated on live CD3+ lymphocytes. The numbers on the plots are the percentages of cells in each quadrant.

FIGS. 6A-6C are graphs which depict experimental data illustrating that T-cells expressing anti-BCMA CARs produce the cytokines IFNγ, IL-2, and TNF in a BCMA-specific manner, as described Example 3. The plots are gated on live CD3+ lymphocytes. The numbers on the plots are the percentages of cells in each quadrant.

FIG. 7A is a graph which depicts experimental data illustrating that T-cells expressing the anti-bcma2 CAR proliferated specifically in response to BCMA. FIG. 7B is a graph which depicts experimental data illustrating that T-cells expressing the SP6 CAR did not proliferate specifically in response to BCMA.

FIGS. 7C and 7D are graphs which depict experimental data illustrating that T-cells from Donor A expressing the anti-bcma2 CAR specifically killed the multiple myeloma cell lines H929 (FIG. 6C) and RPMI8226 (FIG. 6D) in a four-hour cytotoxicity assay at various effector:target cell ratios. T-cells transduced with the negative control SP6 CAR induced much lower levels of cytotoxicity at all effector:target ratios. For all effector:target ratios, the cytotoxicity was determined in duplicate, and the results are displayed as the mean+/− the standard error of the mean.

FIG. 8A is a graph which depicts experimental data illustrating that BCMA is expressed on the surface of primary bone marrow multiple myeloma cells from Myeloma Patient 3, as described in Example 5. The plot is gated on $CD38^{high}$ $CD56^+$ plasma cells, which made up 40% of the bone marrow cells.

FIG. 8B is a graph which depicts experimental data illustrating that allogeneic T-cells transduced with the anti-bcma2 CAR from Donor C produced IFNγ after co-culture with the unmanipulated bone marrow cells of Myeloma Patient 3, as described in Example 5. FIG. 7B also illustrates that T-cells from the same allogeneic donor expressing the anti-bcma2 CAR produced much less IFNγ when they were cultured with peripheral blood mononuclear cell (PBMC) from Myeloma Patient 3. In addition, T-cells from Donor C expressing the SP6 CAR did not specifically recognize the bone marrow of Myeloma Patient 3.

Figure 8A:
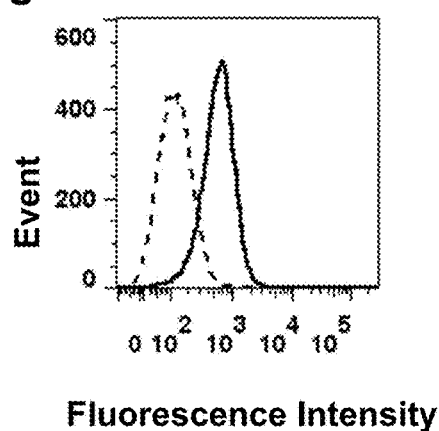
FIG. 8C is a graph which depicts experimental data illustrating that a plasmacytoma resected from Myeloma Patient 1 consisted of 93% plasma cells, and these primary plasma cells expressed BCMA, as revealed by flow cytometry for BCMA (solid line) and isotype-matched control staining (dashed line). The plot is gated on plasma cells.
FIG. 8D is a graph which depicts experimental data illustrating that T-cells from Myeloma Patient 1 expressing the anti-bcma2 CAR produced IFNγ specifically in response to autologous plasmacytoma cells.
Figure 8B:
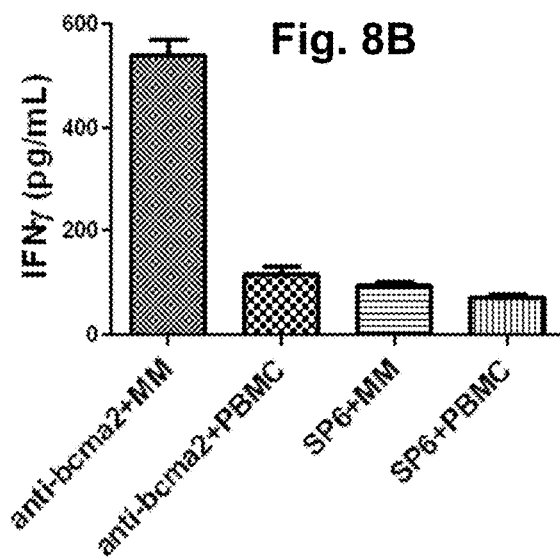
Figure 8C:
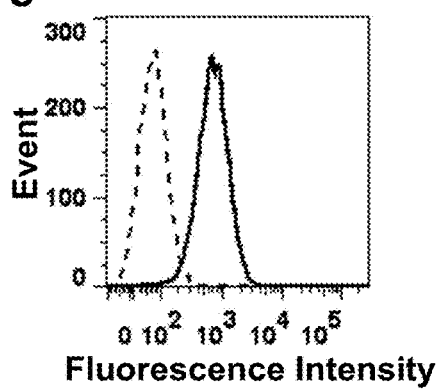
Figure 8D:
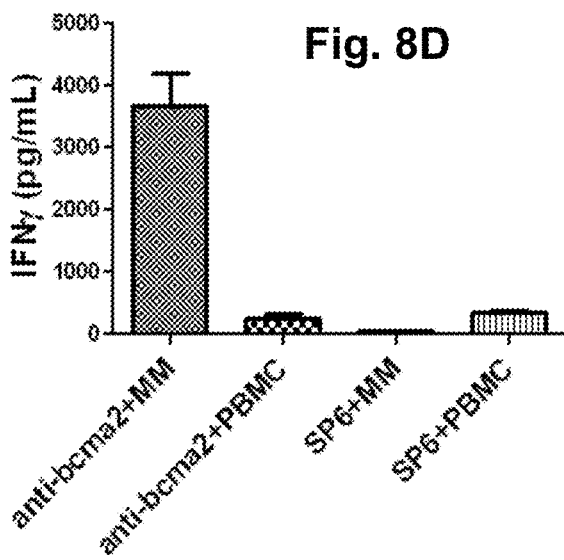
Figure 8E:
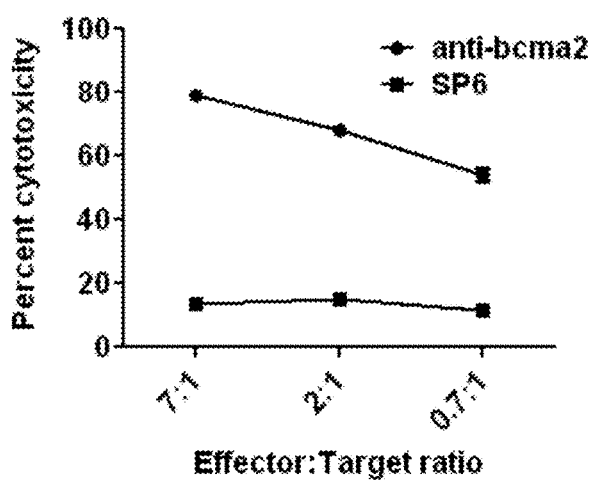

FIG. 8E s a graph which depicts experimental data illustrating that T-cells from Myeloma Patient 1 expressing the anti-bcma2 CAR specifically killed autologous plasmacytoma cells at low effector to target ratios. In contrast, T-cells from Myeloma Patient 1 expressing the SP6 CAR exhibited low levels of cytotoxicity against autologous plasmacytoma cells. For all effector:target ratios, the cytotoxicity was determined in duplicate, and the results are displayed as the mean+/−the standard error of the mean.

Figure 9B:
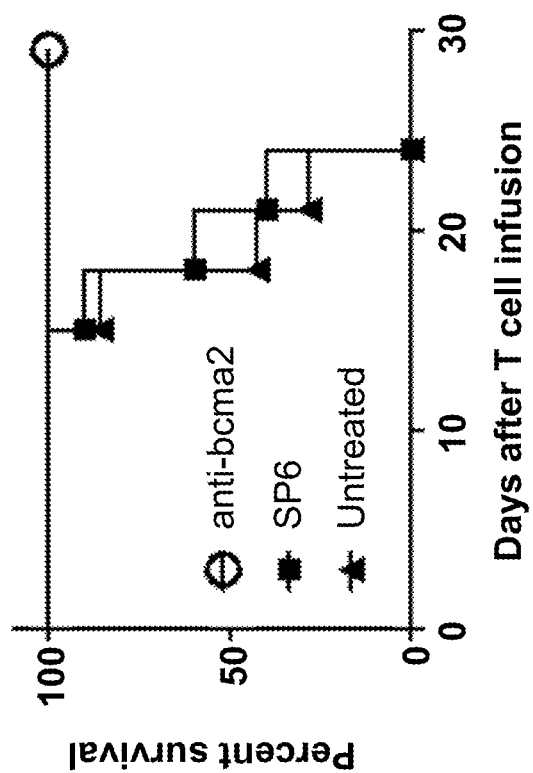
Figure 9A:
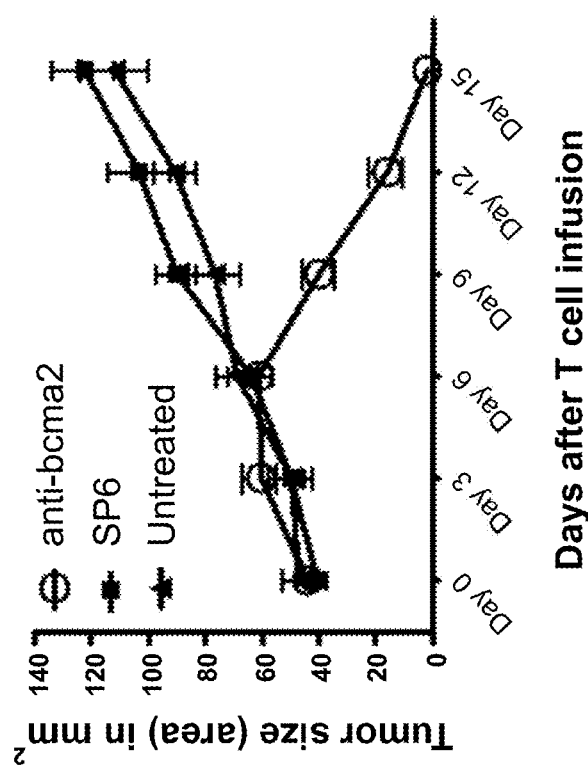

FIG. 9A is a graph which depicts experimental data illustrating that T-cells transduced with the anti-bcma2 CAR can destroy established multiple myeloma tumors in mice. FIG. 9B is a graph which depicts the survival of tumor-bearing mice treated with T-cells expressing the anti-bcma2 CAR as compared to controls.

DETAILED DESCRIPTION OF THE INVENTION

The invention provides an isolated or purified nucleic acid sequence encoding a chimeric antigen receptor (CAR), wherein the CAR comprises an antigen recognition moiety and a T-cell activation moiety. A chimeric antigen receptor (CAR) is an artificially constructed hybrid protein or polypeptide containing an antigen binding domain of an antibody (e.g., a single chain variable fragment (scFv)) linked to T-cell signaling or T-cell activation domains. CARs have the ability to redirect T-cell specificity and reactivity toward a selected target in a non-MHC-restricted manner, exploiting the antigen-binding properties of monoclonal antibodies. The non-MHC-restricted antigen recognition gives T-cells expressing CARs the ability to recognize an antigen independent of antigen processing, thus bypassing a major mechanism of tumor escape. Moreover, when expressed in T-cells, CARs advantageously do not dimerize with endogenous T-cell receptor (TCR) alpha and beta chains.

"Nucleic acid sequence" is intended to encompass a polymer of DNA or RNA, i.e., a polynucleotide, which can be single-stranded or double-stranded and which can contain non-natural or altered nucleotides. The terms "nucleic acid" and "polynucleotide" as used herein refer to a polymeric form of nucleotides of any length, either ribonucleotides (RNA) or deoxyribonucleotides (DNA). These terms refer to the primary structure of the molecule, and thus include double- and single-stranded DNA, and double- and single-stranded RNA. The terms include, as equivalents, analogs of either RNA or DNA made from nucleotide analogs and modified polynucleotides such as, though not limited to methylated and/or capped polynucleotides.

By "isolated" is meant the removal of a nucleic acid from its natural environment. By "purified" is meant that a given nucleic acid, whether one that has been removed from nature (including genomic DNA and mRNA) or synthesized (including cDNA) and/or amplified under laboratory conditions, has been increased in purity, wherein "purity" is a relative term, not "absolute purity." It is to be understood, however, that nucleic acids and proteins may be formulated with diluents or adjuvants and still for practical purposes be isolated. For example, nucleic acids typically are mixed with an acceptable carrier or diluent when used for introduction into cells.

The inventive nucleic acid sequence encodes a CAR which comprises an antigen recognition moiety that is directed against B-cell Maturation Antigen (BCMA, also known as CD269). BCMA is a member of the tumor necrosis factor receptor superfamily (see, e.g., Thompson et al., *J Exp. Medicine,* 192(1): 129-135 (2000), and Mackay et al., *Annu. Rev. Immunol.,* 21: 231-264 (2003)). BCMA binds B-cell activating factor (BAFF) and a proliferation inducing ligand (APRIL) (see, e.g., Mackay et al., supra, and Kalled et al., *Immunological Reviews,* 204: 43-54 (2005)). Among nonmalignant cells, BCMA has been reported to be expressed mostly in plasma cells and subsets of mature B-cells (see, e.g., Laabi et al., *EMBO J.,* 11(11): 3897-3904 (1992); Laabi et al., *Nucleic Acids Res.,* 22(7): 1147-1154 (1994); Kalled et al., supra; O'Connor et al., *J. Exp. Medicine,* 199(1): 91-97 (2004); and Ng et al., *J. Immunol.,* 173(2): 807-817 (2004)). Mice deficient in BCMA are healthy and have normal numbers of B-cells, but the survival of long-lived plasma cells is impaired (see, e.g., O'Connor et al, supra; Xu et al., *Mol. Cell. Biol.,* 21(12): 4067-4074 (2001); and Schiemann et al., *Science,* 293(5537): 2111-2114 (2001)). BCMA RNA has been detected universally in multiple myeloma cells, and BCMA protein has been detected on the surface of plasma cells from multiple myeloma patients by several investigators (see, e.g., Novak et al., *Blood,* 103(2): 689-694 (2004); Neri et al., *Clinical Cancer Research,* 13(19): 5903-5909 (2007); Bellucci et al., *Blood,* 105(10): 3945-3950 (2005); and Moreaux et al., *Blood,* 103(8): 3148-3157 (2004)).

The inventive nucleic acid sequence encodes a CAR which comprises an antigen recognition moiety that contains a monoclonal antibody directed against BCMA, or an antigen-binding portion thereof. The term "monoclonal antibodies," as used herein, refers to antibodies that are produced by a single clone of B-cells and bind to the same epitope. In contrast, "polyclonal antibodies" refer to a population of antibodies that are produced by different B-cells and bind to different epitopes of the same antigen. The antigen recognition moiety of the CAR encoded by the inventive nucleic acid sequence can be a whole antibody or an antibody fragment. A whole antibody typically consists of four polypeptides: two identical copies of a heavy (H) chain polypeptide and two identical copies of a light (L) chain polypeptide. Each of the heavy chains contains one N-terminal variable (VH) region and three C-terminal constant (CH1, CH2 and CH3) regions, and each light chain contains one N-terminal variable (VL) region and one C-terminal constant (CL) region. The variable regions of each pair of light and heavy chains form the antigen binding site of an antibody. The VH and VL regions have the same general structure, with each region comprising four framework regions, whose sequences are relatively conserved. The framework regions are connected by three complementarity determining regions (CDRs). The three CDRs, known as CDR1, CDR2, and CDR3, form the "hypervariable region" of an antibody, which is responsible for antigen binding.

The terms "fragment of an antibody," "antibody fragment," "functional fragment of an antibody," and "antigen-binding portion" are used interchangeably herein to mean one or more fragments or portions of an antibody that retain the ability to specifically bind to an antigen (see, generally, Holliger et al., *Nat. Biotech.,* 23(9): 1126-1129 (2005)). The antigen recognition moiety of the CAR encoded by the inventive nucleic acid sequence can contain any BCMA-binding antibody fragment. The antibody fragment desirably comprises, for example, one or more CDRs, the variable region (or portions thereof), the constant region (or portions thereof), or combinations thereof. Examples of antibody fragments include, but are not limited to, (i) a Fab fragment, which is a monovalent fragment consisting of the VL, VH, CL, and CH1 domains; (ii) a F(ab')2 fragment, which is a bivalent fragment comprising two Fab fragments linked by a disulfide bridge at the hinge region; (iii) a Fv fragment consisting of the VL and VH domains of a single arm of an antibody; (iv) a single chain Fv (scFv), which is a monovalent molecule consisting of the two domains of the Fv fragment (i.e., VL and VH) joined by a synthetic linker which enables the two domains to be synthesized as a single polypeptide chain (see, e.g., Bird et al., *Science,* 242: 423-426 (1988); Huston et al., *Proc. Natl. Acad. Sci. USA,* 85: 5879-5883 (1988); and Osbourn et al., *Nat. Biotechnol.,* 16: 778 (1998)) and (v) a diabody, which is a dimer of polypeptide chains, wherein each polypeptide chain comprises a VH connected to a VL by a peptide linker that is too short to allow pairing between the VH and VL on the same polypeptide chain, thereby driving the pairing between the complementary domains on different VH-VL polypeptide chains to generate a dimeric molecule having two functional antigen binding sites. Antibody fragments are known in the art and are described in more detail in, e.g., U.S. Patent Application Publication 2009/0093024 A1. In a preferred embodiment, the antigen recognition moiety of the CAR encoded by the inventive nucleic acid sequence comprises an anti-BCMA single chain Fv (scFv).

An antigen-binding portion or fragment of a monoclonal antibody can be of any size so long as the portion binds to BCMA. In this respect, an antigen binding portion or fragment of the monoclonal antibody directed against BCMA (also referred to herein as an "anti-BCMA monoclonal antibody") desirably comprises between about 5 and 18 amino acids (e.g., about 5, 6, 7, 8, 9, 10, 11, 12, 13, 14, 15, 16, 17, 18, or a range defined by any two of the foregoing values).

In one embodiment, the inventive nucleic acid sequence encodes an antigen recognition moiety that comprises a variable region of an anti-BCMA monoclonal antibody. In this respect, the antigen recognition moiety comprises a light chain variable region, a heavy chain variable region, or both a light chain variable region and a heavy chain variable region of an anti-BCMA monoclonal antibody. Preferably, the antigen recognition moiety of the CAR encoded by the inventive nucleic acid sequence comprises a light chain variable region and a heavy chain variable region of an anti-BCMA monoclonal antibody. Heavy and light chain monoclonal antibody amino acid sequences that bind to BCMA are disclosed in, e.g., International Patent Application Publication WO 2010/104949.

In another embodiment, the inventive nucleic acid sequence encodes a CAR which comprises a signal sequence. The signal sequence may be positioned at the amino terminus of the antigen recognition moiety (e.g., the variable region of the anti-BCMA antibody). The signal sequence may comprise any suitable signal sequence. In one embodiment, the signal sequence is a human granulocyte-macrophage colony-stimulating factor (GM-CSF) receptor sequence or a CD8α signal sequence.

In another embodiment, the CAR comprises a hinge sequence. One of ordinary skill in the art will appreciate that a hinge sequence is a short sequence of amino acids that facilitates antibody flexibility (see, e.g., Woof et al., *Nat. Rev. Immunol.,* 4(2): 89-99 (2004)). The hinge sequence may be positioned between the antigen recognition moiety (e.g., an anti-BCMA scFv) and the T-cell activation moiety. The hinge sequence can be any suitable sequence derived or obtained from any suitable molecule. In one embodiment, for example, the hinge sequence is derived from the human CD8a molecule or a CD28 molecule.

The inventive nucleic acid sequence encodes a CAR comprising a T-cell activation moiety. The T-cell activation moiety can be any suitable moiety derived or obtained from any suitable molecule. In one embodiment, for example, the T-cell activation moiety comprises a transmembrane domain. The transmembrane domain can be any transmembrane domain derived or obtained from any molecule known in the art. For example, the transmembrane domain can be obtained or derived from a CD8a molecule or a CD28 molecule. CD8 is a transmembrane glycoprotein that serves as a co-receptor for the T-cell receptor (TCR), and is expressed primarily on the surface of cytotoxic T-cells. The most common form of CD8 exists as a dimer composed of a CD8α and CD8β chain. CD28 is expressed on T-cells and provides co-stimulatory signals required for T-cell activation. CD28 is the receptor for CD80 (B7.1) and CD86 (B7.2). In a preferred embodiment, the CD8α and CD28 are human.

In addition to the transmembrane domain, the T-cell activation moiety further comprises an intracellular (i.e., cytoplasmic) T-cell signaling domain. The intercellular T-cell signaling domain can be obtained or derived from a CD28 molecule, a CD3 zeta (ζ) molecule or modified versions thereof, a human Fc receptor gamma (FcRγ) chain, a CD27 molecule, an OX40 molecule, a 4-1BB molecule, or other intracellular signaling molecules known in the art. As discussed above, CD28 is a T-cell marker important in T-cell co-stimulation. CD3ζ associates with TCRs to produce a signal and contains immunoreceptor tyrosine-based activation motifs (ITAMs). 4-1BB, also known as CD137, transmits a potent costimulatory signal to T-cells, promoting differentiation and enhancing long-term survival of T lymphocytes. In a preferred embodiment, the CD28, CD3 zeta, 4-1BB, OX40, and CD27 are human.

The T-cell activation domain of the CAR encoded by the inventive nucleic acid sequence can comprise any one of aforementioned transmembrane domains and any one or more of the aforementioned intercellular T-cell signaling domains in any combination. For example, the inventive nucleic acid sequence can encode a CAR comprising a CD28 transmembrane domain and intracellular T-cell signaling domains of CD28 and CD3 zeta. Alternatively, for example, the inventive nucleic acid sequence can encode a CAR comprising a CD8α transmembrane domain and intracellular T-cell signaling domains of CD28, CD3 zeta, the Fc receptor gamma (FcRγ) chain, and/or 4-1BB.

In one embodiment, the inventive nucleic acid sequence encodes a CAR which comprises, from 5' to 3', a granulocyte-macrophage colony stimulating factor receptor (GM-CSF receptor) signal sequence, an anti-BCMA scFv, the hinge and transmembrane regions of the human CD8α molecule, the cytoplasmic T-cell signaling domain of the human CD28 molecule, and T-cell signaling domain of the human CD3ζ molecule. In another embodiment, the inventive nucleic acid sequence encodes a CAR which comprises, from 5' to 3', a human CD8α signal sequence, an anti-BCMA scFv, the hinge and transmembrane regions of the human CD8α molecule, the cytoplasmic T-cell signaling domain of the human CD28 molecule, and T-cell signaling domain of the human CD3ζ molecule. In another embodiment, the inventive nucleic acid sequence encodes a CAR which comprises, from 5' to 3', a human CD8α signal sequence, an anti-BCMA scFv, the hinge and transmembrane regions of the human CD8α molecule, the cytoplasmic T-cell signaling domain of the human 4-1BB molecule and/or the cytoplasmic T-cell signaling domain of the human OX40 molecule, and T-cell signaling domain of the human CD3ζ molecule. For example, the inventive nucleic acid sequence comprises or consists of the nucleic acid sequence of SEQ ID NO: 1, SEQ ID NO: 2, or SEQ ID NO: 3.

The invention further provides an isolated or purified chimeric antigen receptor (CAR) encoded by the inventive nucleic acid sequence.

The nucleic acid sequence of the invention can encode a CAR of any length, i.e., the CAR can comprise any number of amino acids, provided that the CAR retains its biological activity, e.g., the ability to specifically bind to antigen, detect diseased cells in a mammal, or treat or prevent disease in a mammal, etc. For example, the CAR can comprise 50 or more (e.g., 60 or more, 100 or more, or 500 or more) amino acids, but less than 1,000 (e.g., 900 or less, 800 or less, 700 or less, or 600 or less) amino acids. Preferably, the CAR is about 50 to about 700 amino acids (e.g., about 70, about 80, about 90, about 150, about 200, about 300, about 400, about 550, or about 650 amino acids), about 100 to about 500 amino acids (e.g., about 125, about 175, about 225, about 250, about 275, about 325, about 350, about 375, about 425, about 450, or about 475 amino acids), or a range defined by any two of the foregoing values.

Included in the scope of the invention are nucleic acid sequences that encode functional portions of the CAR described herein. The term "functional portion," when used in reference to a CAR, refers to any part or fragment of the CAR of the invention, which part or fragment retains the biological activity of the CAR of which it is a part (the parent CAR). Functional portions encompass, for example, those parts of a CAR that retain the ability to recognize target cells, or detect, treat, or prevent a disease, to a similar extent, the same extent, or to a higher extent, as the parent CAR. In reference to a nucleic acid sequence encoding the parent CAR, a nucleic acid sequence encoding a functional portion of the CAR can encode a protein comprising, for example, about 10%, 25%, 30%, 50%, 68%, 80%, 90%, 95%, or more, of the parent CAR.

The inventive nucleic acid sequence can encode a functional portion of a CAR that contains additional amino acids at the amino or carboxy terminus of the portion, or at both termini, which additional amino acids are not found in the amino acid sequence of the parent CAR. Desirably, the additional amino acids do not interfere with the biological function of the functional portion, e.g., recognize target cells, detect cancer, treat or prevent cancer, etc. More desirably, the additional amino acids enhance the biological activity of the CAR, as compared to the biological activity of the parent CAR.

The invention also provides nucleic acid sequences encoding functional variants of the aforementioned CAR. The term "functional variant," as used herein, refers to a CAR, a polypeptide, or a protein having substantial or significant sequence identity or similarity to the CAR encoded by the inventive nucleic acid sequence, which functional variant retains the biological activity of the CAR of which it is a variant. Functional variants encompass, for example, those variants of the CAR described herein (the parent CAR) that retain the ability to recognize target cells to a similar extent, the same extent, or to a higher extent, as the parent CAR. In reference to a nucleic acid sequence encoding the parent CAR, a nucleic acid sequence encoding a functional variant of the CAR can be for example, about 10% identical, about 25% identical, about 30% identical, about 50% identical, about 65% identical, about 80% identical, about 90% identical, about 95% identical, or about 99% identical to the nucleic acid sequence encoding the parent CAR.

A functional variant can, for example, comprise the amino acid sequence of the CAR encoded by the inventive nucleic acid sequence with at least one conservative amino acid substitution. The phrase "conservative amino acid substitution" or "conservative mutation" refers to the replacement of one amino acid by another amino acid with a common property. A functional way to define common properties between individual amino acids is to analyze the normalized frequencies of amino acid changes between corresponding proteins of homologous organisms (Schulz, G. E. and Schirmer, R. H., *Principles of Protein Structure*, Springer-Verlag, New York (1979)). According to such analyses, groups of amino acids may be defined where amino acids within a group exchange preferentially with each other, and therefore resemble each other most in their impact on the overall protein structure (Schulz, G. E. and Schirmer, R. H., supra). Examples of conservative mutations include amino acid substitutions of amino acids within the sub-groups above, for example, lysine for arginine and vice versa such that a positive charge may be maintained; glutamic acid for aspartic acid and vice versa such that a negative charge may be maintained; serine for threonine such that a free —OH can be maintained; and glutamine for asparagine such that a free —NH$_2$ can be maintained.

Alternatively or additionally, the functional variants can comprise the amino acid sequence of the parent CAR with at least one non-conservative amino acid substitution. "Non-conservative mutations" involve amino acid substitutions between different groups, for example, lysine for tryptophan, or phenylalanine for serine, etc. In this case, it is preferable for the non-conservative amino acid substitution to not interfere with, or inhibit the biological activity of, the functional variant. The non-conservative amino acid substitution may enhance the biological activity of the functional variant, such that the biological activity of the functional variant is increased as compared to the parent CAR.

The inventive nucleic acid sequence can encode a CAR (including functional portions and functional variants thereof) that comprises synthetic amino acids in place of one or more naturally-occurring amino acids. Such synthetic amino acids are known in the art, and include, for example, aminocyclohexane carboxylic acid, norleucine, α-amino n-decanoic acid, homoserine, S-acetylaminomethyl-cysteine, trans-3- and trans-4-hydroxyproline, 4-aminophenylalanine, 4-nitrophenylalanine, 4-chlorophenylalanine, 4-carboxyphenylalanine, β-phenylserine β-hydroxyphenylalanine, phenylglycine, α-naphthylalanine, cyclohexylalanine, cyclohexylglycine, indoline-2-carboxylic acid, 1,2,3,4-tetrahydroisoquinoline-3-carboxylic acid, aminomalonic acid, aminomalonic acid monoamide, N'-benzyl-N'-methyl-lysine, N',N'-dibenzyl-lysine, 6-hydroxylysine, ornithine, α-aminocyclopentane carboxylic acid, α-aminocyclohexane carboxylic acid, α-aminocycloheptane carboxylic acid, α-(2-amino-2-norbornane)-carboxylic acid, α,γ-diaminobutyric acid, αβ-diaminopropionic acid, homophenylalanine, and α-tert-butylglycine.

The inventive nucleic acid sequence can encode a CAR (including functional portions and functional variants thereof) which is glycosylated, amidated, carboxylated, phosphorylated, esterified, N-acylated, cyclized via, e.g., a disulfide bridge, or converted into an acid addition salt and/or optionally dimerized or polymerized, or conjugated.

In a preferred embodiment, the inventive nucleic acid sequence encodes a CAR that comprises or consists of the amino acid sequence of SEQ ID NO: 4, SEQ ID NO: 5, SEQ ID NO: 6, SEQ ID NO: 8, SEQ ID NO: 9, SEQ ID NO: 10, SEQ ID NO: 11, or SEQ ID NO: 12.

The inventive nucleic acid sequence can be generated using methods known in the art. For example, nucleic acid sequences, polypeptides, and proteins can be recombinantly produced using standard recombinant DNA methodology (see, e.g., Sambrook et al., *Molecular Cloning: A Laboratory Manual*, 3$^{rd}$ ed., Cold Spring Harbor Press, Cold Spring Harbor, NY 2001; and Ausubel et al., *Current Protocols in Molecular Biology*, Greene Publishing Associates and John Wiley & Sons, N Y, 1994). Further, a synthetically produced nucleic acid sequence encoding the CAR can be isolated and/or purified from a source, such as a plant, a bacterium, an insect, or a mammal, e.g., a rat, a human, etc. Methods of isolation and purification are well-known in the art. Alternatively, the nucleic acid sequences described herein can be commercially synthesized. In this respect, the inventive nucleic acid sequence can be synthetic, recombinant, isolated, and/or purified.

The invention also provides a vector comprising the nucleic acid sequence encoding the inventive CAR. The vector can be, for example, a plasmid, a cosmid, a viral vector (e.g., retroviral or adenoviral), or a phage. Suitable vectors and methods of vector preparation are well known in the art (see, e.g., Sambrook et al., supra, and Ausubel et al., supra).

In addition to the inventive nucleic acid sequence encoding the CAR, the vector preferably comprises expression control sequences, such as promoters, enhancers, polyadenylation signals, transcription terminators, internal ribosome entry sites (IRES), and the like, that provide for the expression of the nucleic acid sequence in a host cell. Exemplary expression control sequences are known in the art and described in, for example, Goeddel, *Gene Expression Technology: Methods in Enzymology*, Vol. 185, Academic Press, San Diego, Calif. (1990).

A large number of promoters, including constitutive, inducible, and repressible promoters, from a variety of different sources are well known in the art. Representative sources of promoters include for example, virus, mammal, insect, plant, yeast, and bacteria, and suitable promoters from these sources are readily available, or can be made synthetically, based on sequences publicly available, for example, from depositories such as the ATCC as well as other commercial or individual sources. Promoters can be unidirectional (i.e., initiate transcription in one direction) or bi-directional (i.e., initiate transcription in either a 3' or 5' direction). Non-limiting examples of promoters include, for example, the T7 bacterial expression system, pBAD (araA) bacterial expression system, the cytomegalovirus (CMV) promoter, the SV40 promoter, and the RSV promoter. Inducible promoters include, for example, the Tet system (U.S. Pat. Nos. 5,464,758 and 5,814,618), the Ecdysone inducible system (No et al., *Proc. Natl. Acad. Sci.*, 93: 3346-3351 (1996)), the T-REX™ system (Invitrogen, Carlsbad, CA), LACSWITCH™ System (Stratagene, San Diego, CA), and the Cre-ERT tamoxifen inducible recombinase system (Indra et al., *Nuc. Acid. Res.*, 27: 4324-4327 (1999); *Nuc. Acid. Res.*, 28: e99 (2000); U.S. Pat. No. 7,112,715; and Kramer & Fussenegger, *Methods Mol. Biol.*, 308: 123-144 (2005)).

The term "enhancer" as used herein, refers to a DNA sequence that increases transcription of, for example, a nucleic acid sequence to which it is operably linked. Enhancers can be located many kilobases away from the coding region of the nucleic acid sequence and can mediate the binding of regulatory factors, patterns of DNA methylation, or changes in DNA structure. A large number of enhancers from a variety of different sources are well known in the art and are available as or within cloned polynucleotides (from, e.g., depositories such as the ATCC as well as other commercial or individual sources). A number of polynucleotides comprising promoters (such as the commonly-used CMV promoter) also comprise enhancer sequences. Enhancers can be located upstream, within, or downstream of coding sequences. The term "Ig enhancers" refers to enhancer elements derived from enhancer regions mapped within the immunoglobulin (Ig) locus (such enhancers include for example, the heavy chain (mu) 5' enhancers, light chain (kappa) 5' enhancers, kappa and mu intronic enhancers, and 3' enhancers (see generally Paul W. E. (ed), *Fundamental Immunology*, 3rd Edition, Raven Press, New York (1993), pages 353-363; and U.S. Pat. No. 5,885,827).

The vector also can comprise a "selectable marker gene." The term "selectable marker gene," as used herein, refers to a nucleic acid sequence that allows cells expressing the nucleic acid sequence to be specifically selected for or against, in the presence of a corresponding selective agent. Suitable selectable marker genes are known in the art and described in, e.g., International Patent Application Publications WO 1992/08796 and WO 1994/28143; Wigler et al., *Proc. Natl. Acad. Sci. USA*, 77: 3567 (1980); O'Hare et al., *Proc. Natl. Acad. Sci. USA*, 78: 1527 (1981); Mulligan & Berg, *Proc. Natl. Acad. Sci. USA*, 78: 2072 (1981); Colberre-Garapin et al., *J. Mol. Biol.*, 150: 1 (1981); Santerre et al., *Gene*, 30: 147 (1984); Kent et al., *Science*, 237: 901-903 (1987); Wigler et al., *Cell*, 11: 223 (1977); Szybalska & Szybalski, *Proc. Natl. Acad. Sci. USA*, 48: 2026 (1962); Lowy et al., *Cell*, 22: 817 (1980); and U.S. Pat. Nos. 5,122,464 and 5,770,359.

In some embodiments, the vector is an "episomal expression vector" or "episome," which is able to replicate in a host cell, and persists as an extrachromosomal segment of DNA within the host cell in the presence of appropriate selective pressure (see, e.g., Conese et al., *Gene Therapy*, 11: 1735-1742 (2004)). Representative commercially available episomal expression vectors include, but are not limited to, episomal plasmids that utilize Epstein Barr Nuclear Antigen 1 (EBNA1) and the Epstein Barr Virus (EBV) origin of replication (oriP). The vectors pREP4, pCEP4, pREP7, and pcDNA3.1 from Invitrogen (Carlsbad, CA) and pBK-CMV from Stratagene (La Jolla, CA) represent non-limiting examples of an episomal vector that uses T-antigen and the SV40 origin of replication in lieu of EBNA1 and oriP.

Other suitable vectors include integrating expression vectors, which may randomly integrate into the host cell's DNA, or may include a recombination site to enable the specific recombination between the expression vector and the host cell's chromosome. Such integrating expression vectors may utilize the endogenous expression control sequences of the host cell's chromosomes to effect expression of the desired protein. Examples of vectors that integrate in a site specific manner include, for example, components of the flp-in system from Invitrogen (Carlsbad, CA) (e.g., pcDNA™5/FRT), or the cre-lox system, such as can be found in the pExchange-6 Core Vectors from Stratagene (La Jolla, CA). Examples of vectors that randomly integrate into host cell chromosomes include, for example, pcDNA3.1 (when introduced in the absence of T-antigen) from Invitrogen (Carlsbad, CA), and pCI or pFN10A (ACT) FLEXI™ from Promega (Madison, WI).

Viral vectors also can be used. Representative viral expression vectors include, but are not limited to, the adenovirus-based vectors (e.g., the adenovirus-based Per.C6 system available from Crucell, Inc. (Leiden, The Netherlands)), lentivirus-based vectors (e.g., the lentiviral-based pLP1 from Life Technologies (Carlsbad, CA)), and retroviral vectors (e.g., the pFB-ERV plus pCFB-EGSH from Stratagene (La Jolla, CA)). In a preferred embodiment, the viral vector is a lentivirus vector.

The vector comprising the inventive nucleic acid encoding the CAR can be introduced into a host cell that is capable of expressing the CAR encoded thereby, including any suitable prokaryotic or eukaryotic cell. Preferred host cells are those that can be easily and reliably grown, have reasonably fast growth rates, have well characterized expression systems, and can be transformed or transfected easily and efficiently.

As used herein, the term "host cell" refers to any type of cell that can contain the expression vector. The host cell can be a eukaryotic cell, e.g., plant, animal, fungi, or algae, or can be a prokaryotic cell, e.g., bacteria or protozoa. The host cell can be a cultured cell or a primary cell, i.e., isolated directly from an organism, e.g., a human. The host cell can be an adherent cell or a suspended cell, i.e., a cell that grows in suspension. Suitable host cells are known in the art and include, for instance, DH5α *E. coli* cells, Chinese hamster ovarian cells, monkey VERO cells, COS cells, HEK293 cells, and the like. For purposes of amplifying or replicating the recombinant expression vector, the host cell may be a prokaryotic cell, e.g., a DH5α cell. For purposes of producing a recombinant CAR, the host cell can be a mammalian cell. The host cell preferably is a human cell. The host cell can be of any cell type, can originate from any type of tissue, and can be of any developmental stage. In one embodiment, the host cell can be a peripheral blood lymphocyte (PBL), a peripheral blood mononuclear cell (PBMC), or a natural killer (NK). Preferably, the host cell is a natural killer (NK) cell. More preferably, the host cell is a T-cell. Methods for selecting suitable mammalian host cells and methods for transformation, culture, amplification, screening, and purification of cells are known in the art.

The invention provides an isolated host cell which expresses the inventive nucleic acid sequence encoding the CAR described herein. In one embodiment, the host cell is a T-cell. The T-cell of the invention can be any T-cell, such as a cultured T-cell, e.g., a primary T-cell, or a T-cell from a cultured T-cell line, or a T-cell obtained from a mammal. If obtained from a mammal, the T-cell can be obtained from numerous sources, including but not limited to blood, bone marrow, lymph node, the thymus, or other tissues or fluids. T-cells can also be enriched for or purified. The T-cell preferably is a human T-cell (e.g., isolated from a human). The T-cell can be of any developmental stage, including but not limited to, a $CD4^+/CD8^+$ double positive T-cell, a $CD4^+$ helper T-cell, e.g., $Th_1$ and $Th_2$ cells, a $CD8^+$ T-cell (e.g., a cytotoxic T-cell), a tumor infiltrating cell, a memory T-cell, a naïve T-cell, and the like. In one embodiment, the T-cell is a $CD8^+$ T-cell or a $CD4^+$ T-cell. T-cell lines are available from, e.g., the American Type Culture Collection (ATCC, Manassas, VA), and the German Collection of Microorganisms and Cell Cultures (DSMZ) and include, for example, Jurkat cells (ATCC TIB-152), Sup-T1 cells (ATCC CRL-1942), RPMI 8402 cells (DSMZ ACC-290), Karpas 45 cells (DSMZ ACC-545), and derivatives thereof.

In another embodiment, the host cell is a natural killer (NK) cell. NK cells are a type of cytotoxic lymphocyte that plays a role in the innate immune system. NK cells are defined as large granular lymphocytes and constitute the third kind of cells differentiated from the common lymphoid progenitor which also gives rise to B and T lymphocytes (see, e.g., *Immunobiology*, 5th ed., Janeway et al., eds., Garland Publishing, New York, NY (2001)). NK cells differentiate and mature in the bone marrow, lymph node, spleen, tonsils, and thymus. Following maturation, NK cells enter into the circulation as large lymphocytes with distinctive cytotoxic granules. NK cells are able to recognize and kill some abnormal cells, such as, for example, some tumor cells and virus-infected cells, and are thought to be important in the innate immune defense against intracellular pathogens. As described above with respect to T-cells, the NK cell can be any NK cell, such as a cultured NK cell, e.g., a primary NK cell, or an NK cell from a cultured NK cell line, or an NK cell obtained from a mammal. If obtained from a mammal, the NK cell can be obtained from numerous sources, including but not limited to blood, bone marrow, lymph node, the thymus, or other tissues or fluids. NK cells can also be enriched for or purified. The NK cell preferably is a human NK cell (e.g., isolated from a human). NK cell lines are available from, e.g., the American Type Culture Collection (ATCC, Manassas, VA) and include, for example, NK-92 cells (ATCC CRL-2407), NK92MI cells (ATCC CRL-2408), and derivatives thereof.

The inventive nucleic acid sequence encoding a CAR may be introduced into a cell by "transfection," "transformation," or "transduction." "Transfection," "transformation," or "transduction," as used herein, refer to the introduction of one or more exogenous polynucleotides into a host cell by using physical or chemical methods. Many transfection techniques are known in the art and include, for example, calcium phosphate DNA co-precipitation (see, e.g., Murray E. J. (ed.), *Methods in Molecular Biology*, Vol. 7, Gene Transfer and Expression Protocols, Humana Press (1991)); DEAE-dextran; electroporation; cationic liposome-mediated transfection; tungsten particle-facilitated microparticle bombardment (Johnston, *Nature*, 346: 776-777 (1990)); and strontium phosphate DNA co-precipitation (Brash et al., *Mol. Cell Biol.*, 7: 2031-2034 (1987)). Phage or viral vectors can be introduced into host cells, after growth of infectious particles in suitable packaging cells, many of which are commercially available.

Without being bound to a particular theory or mechanism, it is believed that by eliciting an antigen-specific response against BCMA, the CARs encoded by the inventive nucleic acid sequence provide for one or more of the following: targeting and destroying BCMA-expressing cancer cells, reducing or eliminating cancer cells, facilitating infiltration of immune cells to tumor site(s), and enhancing/extending anti-cancer responses. Thus, the invention provides a method of destroying multiple myeloma cells, which comprises contacting one or more of the aforementioned isolated T-cells or natural killer cells with a population of multiple myeloma cells that express BCMA, whereby the CAR is produced and binds to BCMA on the multiple myeloma cells and the multiple myeloma cells are destroyed. As discussed herein, multiple myeloma, also known as plasma cell myeloma or Kahler's disease, is a cancer of plasma cells, which are a type of white blood cell normally responsible for the production of antibodies (Raab et al., *Lancet*, 374: 324-329 (2009)). Multiple myeloma affects 1-4 per 100,000 people per year. The disease is more common in men, and for yet unknown reasons is twice as common in African Americans as it is in Caucasian Americans. Multiple myeloma is the least common hematological malignancy (14%) and constitutes 1% of all cancers (Raab et al., supra). Treatment of multiple myeloma typically involves high-dose chemotherapy followed by hematopoietic stem cell transplantation (allogenic or autologous); however, a high rate of relapse is common in multiple myeloma patients that have undergone such treatment. As discussed above, BCMA is highly expressed by multiple myeloma cells (see, e.g., Novak et al., supra; Neri et al., supra; Bellucci et al., supra; and Moreaux et al., supra).

One or more isolated T-cells expressing the inventive nucleic acid sequence encoding the anti-BCMA CAR described herein can be contacted with a population of multiple myeloma cells that express BCMA ex vivo, in vivo, or in vitro. "Ex vivo" refers to methods conducted within or on cells or tissue in an artificial environment outside an organism with minimum alteration of natural conditions. In contrast, the term "in vivo" refers to a method that is conducted within living organisms in their normal, intact state, while an "in vitro" method is conducted using components of an organism that have been isolated from its usual biological context. The inventive method preferably involves ex vivo and in vivo components. In this regard, for example, the isolated T-cells described above can be cultured ex vivo under conditions to express the inventive nucleic acid sequence encoding the anti-BCMA CAR, and then directly transferred into a mammal (preferably a human) affected by multiple myeloma. Such a cell transfer method is referred to in the art as "adoptive cell transfer (ACT)," in which immune-derived cells are passively transferred into a new recipient host to transfer the functionality of the donor immune-derived cells to the new host. Adoptive cell transfer methods to treat various types of cancers, including hematological cancers such as myeloma, are known in the art and disclosed in, for example, Gattinoni et al., *Nat. Rev. Immunol.*, 6(5): 383-393 (2006); June, C H, *J. Clin. Invest.*, 117(6): 1466-76 (2007); Rapoport et al., *Blood*, 117(3): 788-797 (2011); and Barber et al., *Gene Therapy*, 18: 509-516 (2011)).

The invention also provides a method of destroying Hodgkin's lymphoma cells. Hodgkin's lymphoma (formerly known as Hodgkin's disease) is a cancer of the immune system that is marked by the presence of a multinucleated cell type called Reed-Sternberg cells. The two major types of Hodgkin's lymphoma include classical Hodgkin's lymphoma and nodular lymphocyte-predominant Hodgkin's lymphoma. Hodgkin's lymphoma currently is treated with radiation therapy, chemotherapy, or hematopoietic stem cell transplantation, with the choice of treatment depending on the age and sex of the patient and the stage, bulk, and histological subtype of the disease. BCMA expression has been detected on the surface of Hodgkin's lymphoma cells (see, e.g., Chiu et al., *Blood*, 109(2): 729-739 (2007)).

When T-cells or NK cells are administered to a mammal, the cells can be allogeneic or autologous to the mammal. In "autologous" administration methods, cells (e.g., blood-forming stem cells or lymphocytes) are removed from a mammal, stored (and optionally modified), and returned back to the same mammal. In "allogeneic" administration methods, a mammal receives cells (e.g., blood-forming stem cells or lymphocytes) from a genetically similar, but not identical, donor. Preferably, the cells are autologous to the mammal.

The T-cells or NK cells desirably are administered to a human in the form of a composition, such as a pharmaceutical composition. Alternatively, the inventive nucleic acid sequence encoding the CAR, or a vector comprising the CAR-encoding nucleic acid sequence, can be formulated into a composition, such as a pharmaceutical composition, and administered to a human. The inventive pharmaceutical composition can comprise a population of T-cells of NK cells that express the inventive CAR. In addition to the inventive nucleic acid sequence, or host cells which express the inventive CAR, the pharmaceutical composition can comprise other pharmaceutically active agents or drugs, such as chemotherapeutic agents, e.g., asparaginase, busulfan, carboplatin, cisplatin, daunorubicin, doxorubicin, fluorouracil, gemcitabine, hydroxyurea, methotrexate, paclitaxel, rituximab, vinblastine, vincristine, etc. In a preferred embodiment, the pharmaceutical composition comprises an isolated T-cell or NK cell which expresses the inventive CAR, more preferably a population of T-cells or NK cells which express the inventive CAR.

The inventive T-cells or NK cells can be provided in the form of a salt, e.g., a pharmaceutically acceptable salt. Suitable pharmaceutically acceptable acid addition salts include those derived from mineral acids, such as hydrochloric, hydrobromic, phosphoric, metaphosphoric, nitric, and sulphuric acids, and organic acids, such as tartaric, acetic, citric, malic, lactic, fumaric, benzoic, glycolic, gluconic, succinic, and arylsulphonic acids, for example, p-toluenesulphonic acid.

The choice of carrier will be determined in part by the particular inventive nucleic acid sequence, vector, or host cells expressing the CAR, as well as by the particular method used to administer the inventive nucleic acid sequence, vector, or host cells expressing the CAR. Accordingly, there are a variety of suitable formulations of the pharmaceutical composition of the invention. For example, the pharmaceutical composition can contain preservatives. Suitable preservatives may include, for example, methylparaben, propylparaben, sodium benzoate, and benzalkonium chloride. A mixture of two or more preservatives optionally may be used. The preservative or mixtures thereof are typically present in an amount of about 0.0001% to about 2% by weight of the total composition.

In addition, buffering agents may be used in the composition. Suitable buffering agents include, for example, citric acid, sodium citrate, phosphoric acid, potassium phosphate, and various other acids and salts. A mixture of two or more buffering agents optionally may be used. The buffering agent or mixtures thereof are typically present in an amount of about 0.001% to about 4% by weight of the total composition.

Methods for preparing administrable (e.g., parenterally administrable) compositions are known to those skilled in the art and are described in more detail in, for example, *Remington: The Science and Practice of Pharmacy*, Lippincott Williams & Wilkins; 21st ed. (May 1, 2005).

The composition comprising the inventive nucleic acid sequence encoding the CAR, or host cells expressing the CAR, can be formulated as an inclusion complex, such as cyclodextrin inclusion complex, or as a liposome. Liposomes can serve to target the host cells (e.g., T-cells or NK cells) or the inventive nucleic acid sequence to a particular tissue. Liposomes also can be used to increase the half-life of the inventive nucleic acid sequence. Many methods are available for preparing liposomes, such as those described in, for example, Szoka et al., *Ann. Rev. Biophys. Bioeng.*, 9: 467 (1980), and U.S. Pat. Nos. 4,235,871, 4,501,728, 4,837,028, and 5,019,369.

The composition can employ time-released, delayed release, and sustained release delivery systems such that the delivery of the inventive composition occurs prior to, and with sufficient time to cause, sensitization of the site to be treated. Many types of release delivery systems are available and known to those of ordinary skill in the art. Such systems can avoid repeated administrations of the composition, thereby increasing convenience to the subject and the physician, and may be particularly suitable for certain composition embodiments of the invention.

The composition desirably comprises the host cells expressing the inventive nucleic acid sequence encoding a CAR, or a vector comprising the inventive nucleic acid sequence, in an amount that is effective to treat or prevent multiple myeloma or Hodgkin's lymphoma. As used herein, the terms "treatment," "treating," and the like refer to obtaining a desired pharmacologic and/or physiologic effect. Preferably, the effect is therapeutic, i.e., the effect partially or completely cures a disease and/or adverse symptom attributable to the disease. To this end, the inventive method comprises administering a "therapeutically effective amount" of the composition comprising the host cells expressing the inventive nucleic acid sequence encoding a CAR, or a vector comprising the inventive nucleic acid sequence. A "therapeutically effective amount" refers to an amount effective, at dosages and for periods of time necessary, to achieve a desired therapeutic result. The therapeutically effective amount may vary according to factors such as the disease state, age, sex, and weight of the individual, and the ability of the CAR to elicit a desired response in the individual. For example, a therapeutically effective amount of CAR of the invention is an amount which binds to BCMA on multiple myeloma cells and destroys them.

Alternatively, the pharmacologic and/or physiologic effect may be prophylactic, i.e., the effect completely or partially prevents a disease or symptom thereof. In this respect, the inventive method comprises administering a "prophylactically effective amount" of the composition comprising the host cells expressing the inventive nucleic acid sequence encoding a CAR, or a vector comprising the inventive nucleic acid sequence, to a mammal that is predisposed to multiple myeloma or Hodgkin's lymphoma. A "prophylactically effective amount" refers to an amount effective, at dosages and for periods of time necessary, to achieve a desired prophylactic result (e.g., prevention of disease onset).

A typical amount of host cells administered to a mammal (e.g., a human) can be, for example, in the range of one million to 100 billion cells; however, amounts below or above this exemplary range are within the scope of the invention. For example, the daily dose of inventive host cells can be about 1 million to about 50 billion cells (e.g., about 5 million cells, about 25 million cells, about 500 million cells, about 1 billion cells, about 5 billion cells, about 20 billion cells, about 30 billion cells, about 40 billion cells, or a range defined by any two of the foregoing values), preferably about 10 million to about 100 billion cells (e.g., about 20 million cells, about 30 million cells, about 40 million cells, about 60 million cells, about 70 million cells, about 80 million cells, about 90 million cells, about 10 billion cells, about 25 billion cells, about 50 billion cells, about 75 billion cells, about 90 billion cells, or a range defined by any two of the foregoing values), more preferably about 100 million cells to about 50 billion cells (e.g., about 120 million cells, about 250 million cells, about 350 million cells, about 450 million cells, about 650 million cells, about 800 million cells, about 900 million cells, about 3 billion cells, about 30 billion cells, about 45 billion cells, or a range defined by any two of the foregoing values).

Therapeutic or prophylactic efficacy can be monitored by periodic assessment of treated patients. For repeated administrations over several days or longer, depending on the condition, the treatment is repeated until a desired suppression of disease symptoms occurs. However, other dosage regimens may be useful and are within the scope of the invention. The desired dosage can be delivered by a single bolus administration of the composition, by multiple bolus administrations of the composition, or by continuous infusion administration of the composition.

The composition comprising the host cells expressing the inventive CAR-encoding nucleic acid sequence, or a vector comprising the inventive CAR-encoding nucleic acid sequence, can be administered to a mammal using standard administration techniques, including oral, intravenous, intraperitoneal, subcutaneous, pulmonary, transdermal, intramuscular, intranasal, buccal, sublingual, or suppository administration. The composition preferably is suitable for parenteral administration. The term "parenteral," as used herein, includes intravenous, intramuscular, subcutaneous, rectal, vaginal, and intraperitoneal administration. More preferably, the composition is administered to a mammal using peripheral systemic delivery by intravenous, intraperitoneal, or subcutaneous injection.

The composition comprising the host cells expressing the inventive CAR-encoding nucleic acid sequence, or a vector comprising the inventive CAR-encoding nucleic acid sequence, can be administered with one or more additional therapeutic agents, which can be coadministered to the mammal. By "coadministering" is meant administering one or more additional therapeutic agents and the composition comprising the inventive host cells or the inventive vector sufficiently close in time such that the inventive CAR can enhance the effect of one or more additional therapeutic agents, or vice versa. In this regard, the composition comprising the inventive host cells or the inventive vector can be administered first, and the one or more additional therapeutic agents can be administered second, or vice versa. Alternatively, the composition comprising the inventive host cells or the inventive vector and the one or more additional therapeutic agents can be administered simultaneously. An example of a therapeutic agent that can be co-administered with the composition comprising the inventive host cells or the inventive vector is IL-2.

Once the composition comprising host cells expressing the inventive CAR-encoding nucleic acid sequence, or a vector comprising the inventive CAR-encoding nucleic acid sequence, is administered to a mammal (e.g., a human), the biological activity of the CAR can be measured by any suitable method known in the art. In accordance with the inventive method, the CAR binds to BCMA on the multiple myeloma cells, and the multiple myeloma cells are destroyed. Binding of the CAR to BCMA on the surface of multiple myeloma cells can be assayed using any suitable method known in the art, including, for example, ELISA and flow cytometry. The ability of the CAR to destroy multiple myeloma cells can be measured using any suitable method known in the art, such as cytotoxicity assays described in, for example, Kochenderfer et al., *J. Immunotherapy*, 32(7): 689-702 (2009), and Herman et al. *J. Immunological Methods*, 285(1): 25-40 (2004). The biological activity of the CAR also can be measured by assaying expression of certain cytokines, such as CD107a, IFNγ, IL-2, and TNF.

One of ordinary skill in the art will readily appreciate that the inventive CAR-encoding nucleic acid sequence can be modified in any number of ways, such that the therapeutic or prophylactic efficacy of the CAR is increased through the modification. For instance, the CAR can be conjugated either directly or indirectly through a linker to a targeting moiety. The practice of conjugating compounds, e.g., the CAR, to targeting moieties is known in the art. See, for instance, Wadwa et al., *J. Drug Targeting* 3: 111 (1995), and U.S. Pat. No. 5,087,616.

The following examples further illustrate the invention but, of course, should not be construed as in any way limiting its scope.

Example 1

This example demonstrates the expression pattern of BCMA in human cells.

Quantitative polymerase chain reaction (qPCR) was performed on a panel of cDNA samples from a wide range of normal tissues included in the Human Major Tissue qPCR panel II (Origine Technologies, Rockville, MD) using a BCMA-specific primer and probe set (Life Technologies, Carlsbad, CA). cDNA from cells of a plasmacytoma that was resected from a patient with advanced multiple myeloma was analyzed as a positive control. RNA was extracted from the plasmacytoma cells with an RNeasy mini kit (Qiagen, Inc., Valencia, CA), and cDNA was synthesized using standard methods. A standard curve for the BCMA qPCR was created by diluting a plasmid that encoded the full-length BCMA cDNA (Origine Technologies, Rockville, MD) in carrier DNA. The qPCR accurately detected copy numbers from $10^2$ to $10^9$ copies of BCMA per reaction. The number of β-actin cDNA copies in the same tissues was quantitated with a Taqman β-actin primer and probe kit (Life Technologies, Carlsbad, CA). A β-actin standard curve was created by amplifying serial dilutions of a β-actin plasmid. All qPCR reactions were carried out on the Roche LightCycler480 machine (Roche Applied Sciences, Indianapolis, IN).

The results of the qPCR analysis are depicted in FIGS. 1A and 1B. 93% percent of the cells from the plasmacytoma sample were plasma cells as determined by flow cytometry. BCMA expression in the plasmacytoma sample was dramatically higher than BCMA expression in any other tissue. BCMA cDNA was detected in several hematologic tissues, such as peripheral blood mononuclear cells (PBMC), bone marrow, spleen, lymph node, and tonsil. Low levels of BCMA cDNA were detected in most gastrointestinal organs, such as duodenum, rectum, and stomach. BCMA expression in gastrointestinal organs may be the result of plasma cells and B-cells present in gut-associated lymphoid tissues such as the lamina propria and Peyer's Patches (see, e.g., Brandtzaeg, *Immunological Investigations*, 39(4-5): 303-355 (2010)). Low levels of BCMA cDNA also were detected in the testis and the trachea. The low levels of BCMA cDNA detected in the trachea may be due to the presence of plasma cells in the lamina propria of the trachea (see, e.g., Soutar, *Thorax*, 31(2):158-166 (1976)).

The expression of BCMA on the surface of various cell types was further characterized using flow cytometry (see FIGS. 2A-2L), including multiple myeloma cell lines H929, U266, and RPMI8226. The multiple myeloma cell lines H929, U266, and RPMI8226 all expressed cell surface BCMA. In contrast, the sarcoma cell line TC71, the T-cell leukemia line CCRF-CEM, and the kidney cell line 293T-17 did not express cell surface BCMA. Primary CD34$^+$ hematopoietic cells, primary small airway epithelial cells, primary bronchial epithelial cells, and primary intestinal epithelial cells all lacked cell surface BCMA expression.

The results of this example demonstrate that BCMA is expressed on the surface of multiple myeloma cells, and it has a restricted expression pattern in normal tissues.

Example 2

This example describes the construction of the inventive nucleic acid sequence encoding anti-BCMA chimeric antigen receptors (CARs).

Antibody sequences of two mouse-anti-human-BCMA antibodies designated as "C12A3.2" and "C11D5.3" were obtained from International Patent Application Publication WO 2010/104949 (Kalled et al.). The amino acid sequences of the heavy chain variable regions and light chain variable regions of these antibodies were used to design single chain variable fragments (scFvs) having the following general structure:

light chain variable region-linker-heavy chain variable region.

The linker had the following amino acid sequence: GST-SGSGKPGSGEGSTKG (SEQ ID NO: 7) (see, e.g., Cooper et al., *Blood*, 101(4): 1637-1644 (2003)).

Figure 2A:
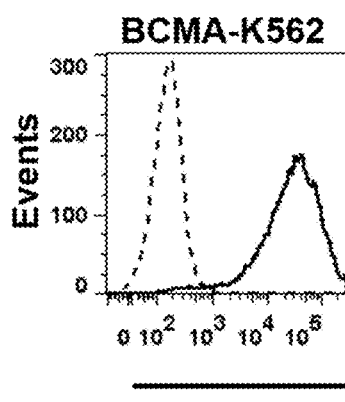
Figure 2B:
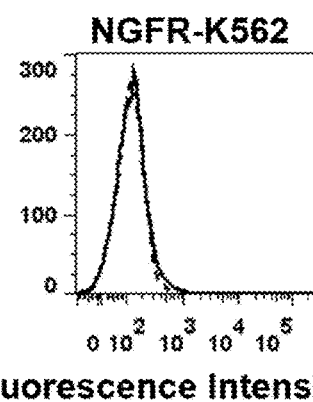
Figure 2C:
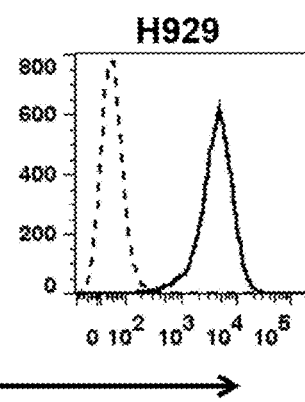
Figure 2D:
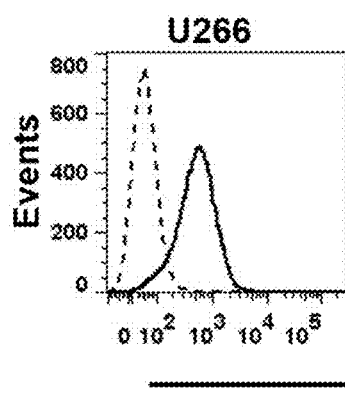
Figure 2E:
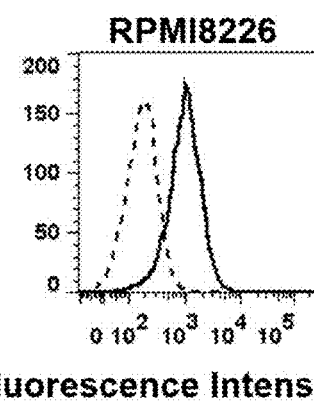
Figure 2F:
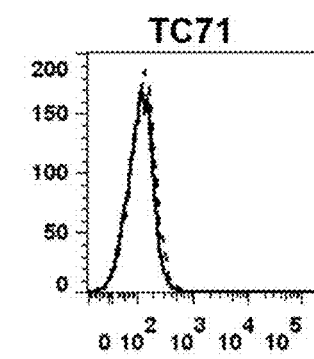
Figure 2G:
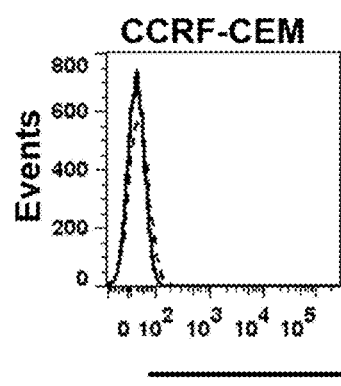
Figure 2H:
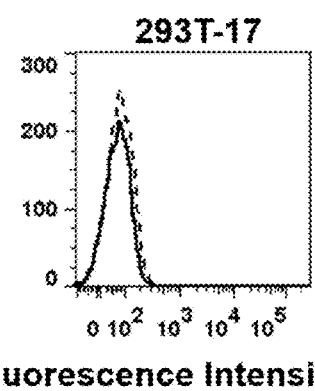
Figure 2I:
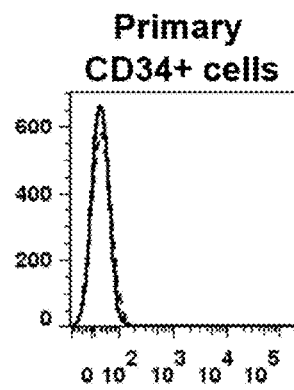
Figure 2J:
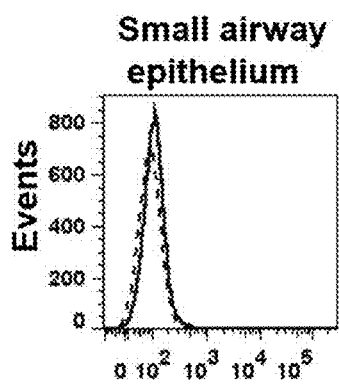
Figure 2K:
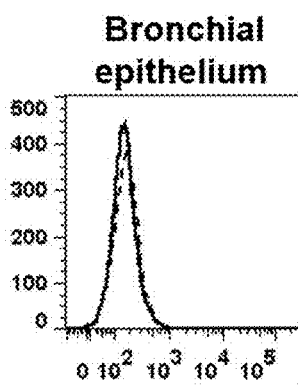
Figure 2L:
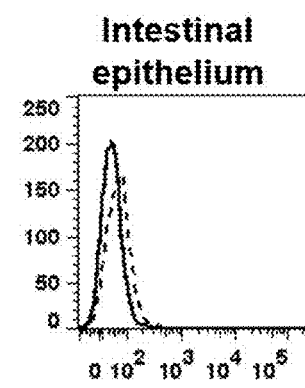
Figure 3A:

DNA sequences encoding two chimeric antigen receptors were designed, each of which contained the following elements from 5' to 3': the CD8α signal sequence, the aforementioned anti-BCMA scFv, hinge and transmembrane regions of the human CD8α molecule, the cytoplasmic portion of the CD28 molecule, and the cytoplasmic portion of the CD3ζ molecule. A schematic of these CAR-encoding nucleic acid sequences is set forth in FIG. 3A. The CARs incorporating variable regions from C12A3.2 and C11D5.3 were designated anti-bcma1 and anti-bcma2, respectively.

DNA sequences encoding five additional chimeric antigen receptors based on the above-described anti-bcma2 CAR were designed, each of which contained different signal sequences and T-cell activation domains. In this respect, 8ss-anti-bcma2 CAR contained the following elements from 5' to 3: the CD8α signal sequence, scFv, hinge and transmembrane regions of the human CD8α molecule, the cytoplasmic portion of the CD28 molecule, and the cytoplasmic portion of the CD3ζ molecule. The G-anti-bcma2 CAR contained the following elements from 5' to 3': the human GM-CSF receptor signal sequence, scFv, hinge and transmembrane regions of the human CD8α molecule, the cytoplasmic portion of the CD28 molecule, and the cytoplasmic portion of the CD3ζ molecule. The anti-bcma2-BB CAR contained the following elements from 5' to 3': the CD8α signal sequence, scFv, hinge and transmembrane regions of the human CD8α molecule, the cytoplasmic portion of the 4-1BB molecule, and the cytoplasmic portion of the CD3ζ molecule. The anti-bcma2-OX40 CAR contained the following elements from 5' to 3': the CD8α signal sequence, scFv, hinge and transmembrane regions of the human CD8α molecule, the cytoplasmic portion of the OX40 molecule (see, e.g., Latza et al., *European Journal of Immunology*, 24: 677-683 (1994)), and the cytoplasmic portion of the CD3ζ molecule. The anti-bcma2-BBOX40 contained the following elements from 5' to 3': the CD8α signal sequence, scFv, hinge and transmembrane regions of the human CD8α molecule, the cytoplasmic portion of the 4-1BB molecule, the cytoplasmic region of the OX40 molecule, and the cytoplasmic portion of the CD3ζ molecule. The elements present in each of the seven CAR sequences are set forth in Table 1.

TABLE 1

| CAR | SEQ ID NO (amino acid) | Signal Sequence | Hinge and Transmembrane Regions | Intracellular T-cell Signaling Domain |
|---|---|---|---|---|
| anti-bcma1 | 4 | Human CD8α | Human CD8α | CD28 CD3ζ |
| anti-bcma2 | 5 | Human CD8α | Human CD8α | CD28 CD3ζ |
| G-Anti-bcma2 | 8 | GM-CSF receptor | Human CD8α | CD28 CD3ζ |
| 8ss-anti-bcma2 | 9 | Human CD8α | Human CD8α | CD28 CD3ζ |
| anti-bcma2-BB | 10 | Human CD8α | Human CD8α | 4-1BB CD3ζ |
| anti-bcma2-OX40 | 11 | Human CD8α | Human CD8α | OX40 CD3ζ |
| anti-bcma2-BBOX40 | 12 | Human CD8α | Human CD8α | 4-1BB OX40 CD3ζ |

The sequences used for CD8a, CD28, CD3ζ, 4-1BB (CD137), and OX40 (CD134) were obtained from the publicly available National Center for Biotechnology Information (NCBI) database.

The CAR-encoding nucleic acid sequences were generated using methods known in the art, such as those described in, for example, Kochenderfer et al., *J. Immunology*, 32(7): 689-702 (2009), and Zhao et al., *J. Immunology*, 183(9): 5563-5574 (2009). The nucleic acid sequence encoding each CAR was codon optimized and synthesized using GeneArt™ technology (Life Technologies, Carlsbad, CA) with appropriate restriction sites.

The sequences encoding the anti-bcma1 and anti-bcma2 CARs were ligated into a lentiviral vector plasmid designated pRRLSIN.cPPT.MSCV.coDMF5.oPRE (see, e.g., Yang et al., *J. Immunotherapy*, 33(6): 648-658 (2010)). The coDMF5 portion of this vector was replaced with the CAR-encoding nucleic acid sequences using standard methods. The two resulting anti-BCMA CAR vectors were denoted pRRLSIN.cPPT.MSCV.anti-bcma1.oPRE and pRRLSIN.cPPT.MSCV.anti-bcma2.oPRE. A negative-control CAR containing the SP6 scFv that recognizes the hapten 2,4,6-trinitrophenyl also was constructed (see, e.g., Gross et al., *Proc. Natl. Acad. Sci. USA*, 86(24): 10024-10028 (1989)). This CAR was referred to as SP6. The SP6 CAR was cloned into the same lentiviral vector as the anti-BCMA CARs and contained the same signaling domains as anti-bcma1 and anti-bcma2. Supernatant containing lentiviruses encoding each CAR was produced by the protocol described in Yang et al., supra. Specifically, 293T-17 cells (ATCC CRL-11268) were transfected with the following plasmids: pMDG (encoding the vesicular stomatitis virus envelope protein), pMDLg/pRRE (encoding HIV Gag and Pol proteins), pRSV-Rev (encoding RSV Rev protein), and plasmids encoding the anti-bcma CARs (see, e.g., Yang et al., supra).

The sequences encoding the G-anti-bcma2, 8ss-anti-bcma2, anti-bcma2-BB, anti-bcma2-OX40, and anti-bcma2-BBOX40 CARs were each ligated into a gammaretroviral vector plasmid designated MSGV (mouse stem cell virus-based splice-gag vector) using standard methods, such as those described in, e.g., Hughes et al., *Human Gene Therapy*, 16: 457-472 (2005). After the CAR-encoding gammaretroviral plasmids were generated, replication incompetent retroviruses with the RD114 envelope were produced by transient transfection of 293-based packaging cells as described in Kochenderfer et al., *J. Immunotherapy*, 32(7): 689-702 (2009).

The replication-incompetent lentiviruses and retroviruses encoding the above-described CARs were used to transduce human T-cells. For anti-bcma1 and anti-bcma2, T-cells were cultured as described previously (see, e.g., Kochenderfer et al., *J. Immunotherapy*, 32(7): 689-702 (2009)) and were stimulated with the anti-CD3 monoclonal antibody OKT3

Figure 3B:
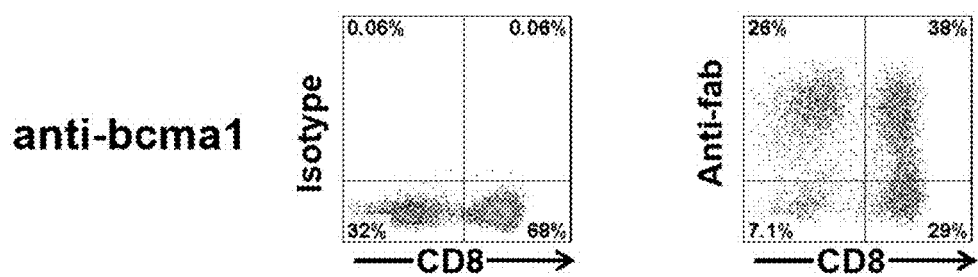
Figure 3C:
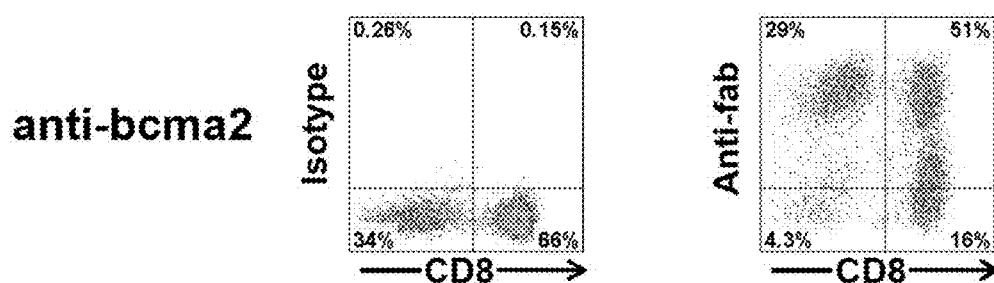
Figure 3D:
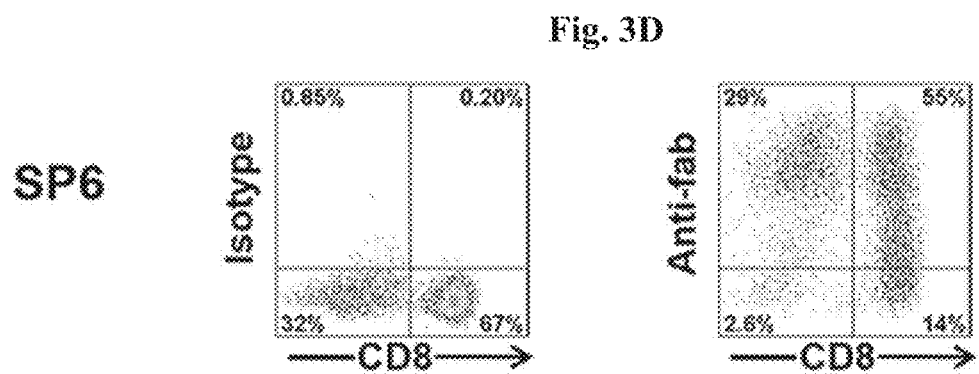

(Ortho-Biotech, Horsham, PA) in AIM V™ medium (Life Technologies, Carlsbad, CA) containing 5% human AB serum (Valley Biomedical, Winchester, VA) and 300 international units (IU)/mL of interleukin-2 (Novartis Diagnostics, Emeryville, CA). Thirty-six hours after the cultures were started, the activated T-cells were suspended in lentiviral supernatant with protamine sulfate and 300 IU/mL IL-2. The cells were centrifuged for 1 hour at 1200×g. The T-cells were then cultured for three hours at 37° C. The supernatant was then diluted 1:1 with RPMI medium (Mediatech, Inc., Manassas, VA)+10% fetal bovine serum (Life Technologies, Carlsbad, CA) and IL-2. The T-cells were cultured in the diluted supernatant overnight, and then returned to culture in AIM V™ medium (Life Technologies, Carlsbad, CA) plus 5% human AB serum with IL-2. T-cells were stained with biotin-labeled polyclonal goat anti-mouse-F(ab)$_2$ antibodies (Jackson Immunoresearch Laboratories, Inc., West Grove, PA) to detect the anti-BCMA CARs. High levels of cell surface expression of the anti-bcma1 CAR, the anti-bcma2 CAR, and the SP6 CAR on the transduced T-cells were observed, as shown in FIGS. 3B-3D.

For the G-anti-bcma2, 8ss-anti-bcma2, anti-bcma2-BB, anti-bcma2-OX40, and anti-bcma2-BBOX40 CARs, peripheral blood mononuclear cells were suspended at a concentration of 1×10$^6$ cell per mL in T-cell medium containing 50 ng/mL of the anti-CD3 monoclonal antibody OKT3 (Ortho, Bridgewater, NJ) and 300 IU/mL of IL-2. RETRONECTIN™ polypeptide (Takara Bio Inc., Shiga, Japan), which is a recombinant polypeptide of human fibronectin fragments that binds viruses and cell surface proteins, was dissolved at a concentration of 11 μg/mL in phosphate buffered saline (PBS) solution, and two mL of the RETRONECTIN™ polypeptide in PBS solution were added to each well of nontissue-culture-coated 6 well plates (BD Biosciences, Franklin Lakes, New Jersey). The plates were incubated for two hours at room temperature (RT). After the incubation, the RETRONECTIN™ solution was aspirated, and 2 mL of a blocking solution consisting of Hanks' balanced salt solution (HBSS) plus 2% bovine serum albumin (BSA) were added to each RETRONECTIN™-coated well. The plates were incubated for 30 minutes at room temperature (RT). The blocking solution was aspirated, and the wells were rinsed with a solution of HBSS+2.5% (4-(2-hydroxyethyl)-1-piperazineethanesulfonic acid) (HEPES). Retroviral supernatant was rapidly thawed and diluted 1:1 in T-cell media, and two mL of the diluted supernatant were then added to each RETRONECTIN™-coated well. After addition of the supernatants, the plates were centrifuged at 2000×g for 2 hours at 32° C. The supernatant was then aspirated from the wells, and 2×10$^6$ T-cells that had been cultured with OKT3 antibody and IL-2 for 2 days were added to each well. When the T-cells were added to the retrovirus-coated plates, the T-cells were suspended at a concentration of 0.5×10$^6$ cells per mL in T-cell medium plus 300 IU/mL of IL-2. After the T-cells were added to each well, the plates were centrifuged for 10 minutes at 1000×g.

The plates were incubated at 37° C. overnight. The transduction was repeated the next day. After an 18-24 hour incubation, the T-cells were removed from the plates and suspended in fresh T-cell medium with 300 IU/mL of IL-2 at a concentration of 0.5×10$^6$ cells per mL and cultured at 37° C. and 5% CO$_2$. High levels of cell surface expression of anti-bcma2-BBOX40, anti-bcma2-BB, and 8ss-anti-bcma2 on the transduced T-cells were observed.

The results of this example demonstrate a method of producing the inventive CAR-encoding nucleic acid sequence, and methods of expressing the CAR on the surface of T-cells.

Example 3

This example describes a series of experiments used to determine the specificity of the inventive CAR for BCMA.
Cells NCI-H929, U266, and RPMI8226 are all BCMA+ multiple myeloma cell lines that were obtained from ATCC (ATCC Nos. CRL-9068, TIB-196, and CCL-155, respectively). A549 (ATCC No. CCL-185) is a BCMA-negative lung cancer cell line. TC71 is a BCMA-negative sarcoma cell line. CCRF-CEM is a BCMA-negative T-cell line (ATCC No. CCL-119). BCMA-K562 are K562 cells (ATCC No. CCL-243) that have been transduced with a nucleic acid sequence encoding full-length BCMA. NGFR-K562 are K562 cells that have been transduced with the gene encoding low-affinity nerve growth factor (see, e.g., Kochenderfer et al., *J. Immunotherapy.*, 32(7):689-702 (2009)). Peripheral blood lymphocytes (PBL) from three patients with multiple myeloma (i.e., Myeloma Patient 1 through 3) were used, as were PBL from three other subjects: Donor A, Donor B, and Donor C. Donors A through C all had melanoma. CD34+ primary cells were obtained from three normal healthy donors. A sample of plasmacytoma cells was obtained from Myeloma patient 1, and a sample of bone marrow was obtained from Myeloma Patient 3. All of the human samples mentioned above were obtained from patients enrolled in IRB-approved clinical trials at the National Cancer Institute. The following primary human epithelial cells were obtained from Lonza, Inc. (Basel, Switzerland): small airway epithelial cells, bronchial epithelial cells, and intestinal epithelial cells.

Interferon-γ and TNF ELISA

BCMA-positive or BCMA-negative cells were combined with CAR-transduced T-cells in duplicate wells of a 96 well round bottom plate (Corning Life Sciences, Lowell, MA) in AIM V™ medium (Life Technologies, Carlsbad, CA)+5% human serum. The plates were incubated at 37° C. for 18-20 hours. Following the incubation, ELISAs for IFNγ and TNF were performed using standard methods (Pierce, Rockford, IL).

T-cells transduced with the anti-bcma1 or anti-bcma2 CARs produced large amounts of IFNγ when they were cultured overnight with the BCMA-expressing cell line BCMA-K562, but the CAR-transduced T-cells only produced background levels of IFNγ when they were cultured with the negative control cell line NGFR-K562, as indicated in Table 2 (all units are pg/mL IFNγ).

TABLE 2

| | BCMA-Expressing Targets** | | | BCMA-Negative Targets | | | | | T-cells |
|---|---|---|---|---|---|---|---|---|---|
| | BCMA-K562 | H929 | RPMI-8226 | NGFR-K562 | CCRF-CEM | A549 | TC71 | 293T | Alone |
| Effector Cells* | | | | | | | | | |
| anti-bcma1 | 15392 | 11306 | 5335 | 76 | 76 | 52 | 65 | 54 | 112 |
| anti-bcma2 | 25474 | 23120 | 10587 | 62 | 67 | 32 | 31 | 28 | 41 |
| SP6 | 32 | 60 | 149 | 27 | 28 | 21 | 361 | 73 | 27 |

TABLE 2-continued

| | BCMA-Expressing Targets** | | | BCMA-Negative Targets | | | | | T-cells |
| --- | --- | --- | --- | --- | --- | --- | --- | --- | --- |
| | BCMA-K562 | H929 | RPMI-8226 | NGFR-K562 | CCRF-CEM | A549 | TC71 | 293T | Alone |
| Untransduced | <12 | <12 | <12 | <12 | <12 | <12 | <12 | 12 | <12 |
| Targets Alone | <12 | <12 | <12 | <12 | <12 | <12 | <12 | 13 | |

*Effector cells were T-cells from a patient with multiple myeloma (Myeloma Patient 2). The T-cells were transduced with the indicated CAR or left untransduced.
**The indicated target cells were combined with the effector cells for an overnight incubation and an IFNγ ELISA was performed.

T-cells expressing the 8ss-anti-bcma2, anti-bcma2-BB, and anti-bcma2-OX40 CARs produced IFNγ specifically in response to BCMA+ target cells when T-cells and target cells were cocultured overnight, as indicated in Table 3 (all units are pg/mL of IFNγ).

TABLE 3

| | BCMA-Positive Targets | | BCMA-Negative Targets | | | |
| --- | --- | --- | --- | --- | --- | --- |
| | BCMA-K562 | RPMI-8226 | NGFR-K562 | CCRF-CEM | A549 | T-cells Alone |
| Effector Cells | | | | | | |
| anti-bcma2-OX40 | 17704 | 4875 | 42 | 44 | 24 | 40 |
| anti-bcma2-BB | 25304 | 8838 | 404 | 602 | 350 | 706 |
| 8ss-anti-bcma2 | 9671 | 2168 | 100 | 120 | 49 | 171 |
| Untransduced | <12 | 57 | 15 | 17 | <12 | 20 |

T-cells transduced with anti-BCMA CARs produced large amounts of IFNγ when they were cultured overnight with BCMA-expressing multiple myeloma cell lines. In contrast, the anti-BCMA CARs produced much lower amounts of IFNγ when they were cultured with a variety of BCMA-negative cell lines. Compared with T-cells transduced with the anti-bcma1 CAR, T-cells transduced with the anti-bcma2 CAR and variants thereof (i.e., 8ss-anti-bcma2, anti-bcma2-BB, and anti-bcma2-OX40) produced more IFNγ when cultured with BCMA-positive cells and less IFNγ when cultured with BCMA-negative cells.

T-cells transduced with the anti-bcma2 CAR variants produced TNF specifically in response to BCMA+ target cells when T-cells and target cells were cocultured overnight, as indicated in Table 4 (all units are pg/mL of tumor necrosis factor (TNF)).

TABLE 4

| | BCMA-Positive Targets | | BCMA-Negative Targets | | | |
| --- | --- | --- | --- | --- | --- | --- |
| | BCMA-K562 | RPMI-8226 | NGFR-K562 | CCRF-CEM | A549 | T-cells Alone |
| Effector Cells | | | | | | |
| anti-bcma2-OX40 | 4913 | 3406 | <40 | 47 | <40 | 74 |
| anti-bcma2-BB | 6295 | 2723 | 56 | 164 | 89 | 252 |
| 8ss-anti-bcma2 | 5340 | 1354 | <40 | 121 | <40 | 191 |
| Untransduced | <40 | <40 | 47 | <40 | <40 | <40 |

Because the T-cells transduced with the anti-bcma2 CAR and variants thereof exhibited slightly stronger and more specific recognition of BCMA-expressing cells than T-cells transduced with the anti-bcma1 CAR, only the anti-bcma2 CAR and anti-bcma2 CAR variants were used in the following experiments.

CD107a Assay

Two populations of T-cells were prepared in two separate tubes. One tube contained BCMA-K562 cells, and the other tube contained NGFR-K562 cells. Both tubes also contained T-cells transduced with the anti-bcma2 CAR and anti-bcma2 CAR variants, 1 mL of AIM V™ medium (Life Technologies, Carlsbad, CA)+5% human serum, a titrated concentration of an anti-CD107a antibody (eBioscience, Inc., San Diego, CA; clone eBioH4A3), and 1 μL of Golgi Stop (BD Biosciences, Franklin Lakes, NJ). All tubes were incubated at 37° C. for four hours and then stained for expression of CD3, CD4, and CD8.

Figure 4A:
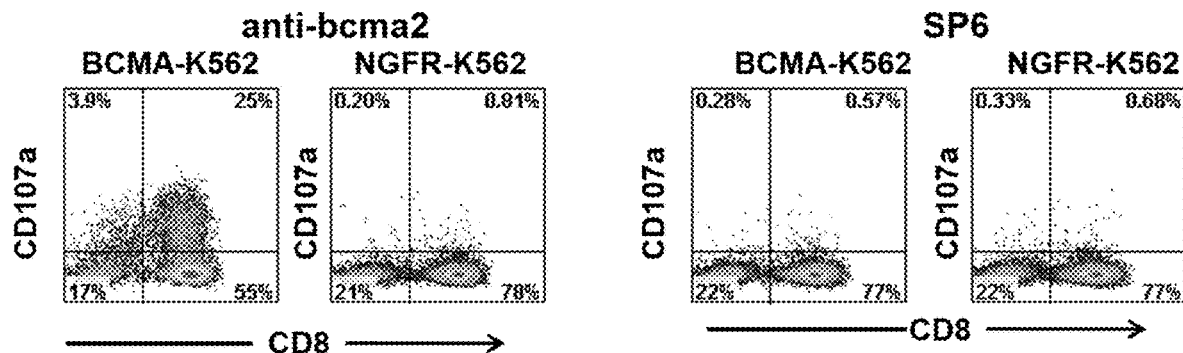
Figure 4B:
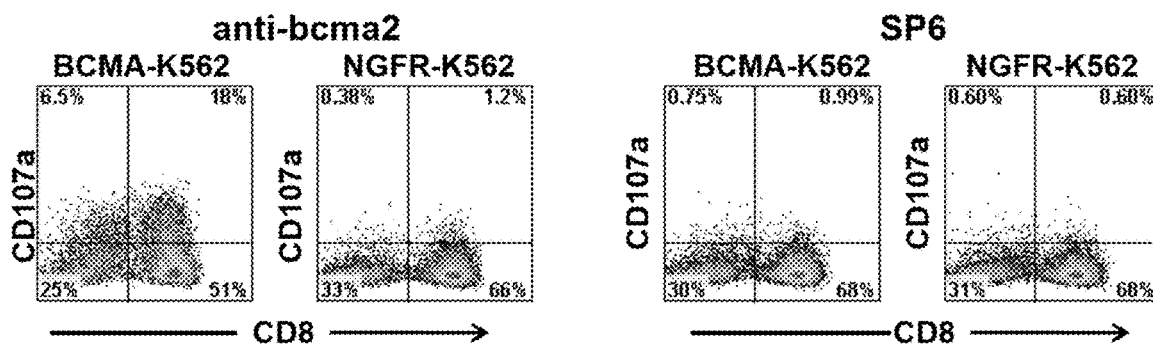
Figure 4C:
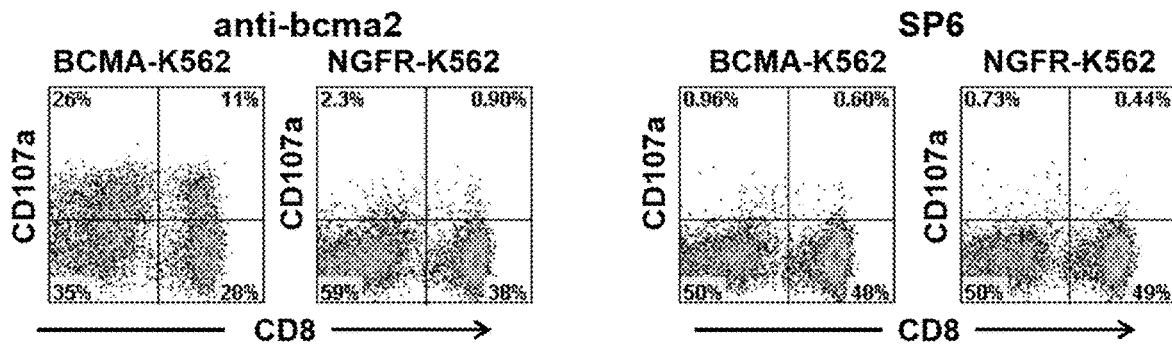

CAR-transduced T-cells from three different subjects unregulated CD107a specifically in response to stimulation with BCMA-expressing target cells (see FIGS. 4A-4C). This indicates the occurrence of BCMA-specific degranulation of the T-cells, which is a prerequisite for perforin-mediated cytotoxicity (see, e.g., Rubio et al., Nature Medicine, 9(11): 1377-1382 (2003)). In addition, T-cells expressing the anti-bcma2 CAR variants 8ss-anti-bcma2, anti-bcma2-BB, anti-bcma2-OX40 degranulated in a BCMA-specific manner when stimulated with target cells in vitro as shown in FIGS. 5A-5D.

Intracellular Cytokine Staining Assay (ICCS)

A population of BCMA-K562 cells and a population of NGFR-K562 cells were prepared in two separate tubes as described above. Both tubes also contained T-cells transduced with the anti-bcma2 CAR from Myeloma Patient 2, 1 mL of AIM V medium (Life Technologies, Carlsbad, CA)+ 5% human serum, and 1 μL of Golgi Stop (BD Biosciences, Franklin Lakes, NJ). All tubes were incubated at 37° C. for six hours. The cells were surface-stained with anti-CD3, anti-CD4, and anti-CD8 antibodies. The cells were permeabilized, and intracellular staining was conducted for IFNγ

(BD Biosciences, Franklin Lakes, NJ, clone B27), IL-2 (BD Biosciences, Franklin Lakes, NJ, clone MQ1-17H12), and TNF (BD Biosciences, Franklin Lakes, NJ, clone MAb11) by following the instructions of the Cytofix/Cytoperm kit (BD Biosciences, Franklin Lakes, NJ).

Large populations of T-cells transduced with the anti-bcma2 CAR from Myeloma Patient 2 specifically produced the cytokines IFNγ, IL-2, and TNF in a BCMA-specific manner after the six-hour stimulation with BCMA-expressing target cells, as shown in FIGS. 6A-6C.

Proliferation Assays

The ability of T-cells transduced with the anti-bcma2 CAR to proliferate when stimulated with BCMA-expressing target cells was assessed. Specifically, $0.5 \times 10^6$ irradiated BCMA-K562 cells or $0.5 \times 10^6$ irradiated NGFR-K562 cells were co-cultured with $1 \times 10^6$ total T-cells that had been transduced with either the anti-bcma2 CAR or the SP6 CAR. The T-cells were labeled with carboxyfluorescein diacetate succinimidyl ester (CFSE) (Life Technologies, Carlsbad, CA) as described in Mannering et al., J. Immunological Methods, 283(1-2): 173-183 (2003). The medium used in the co-cultures was AIM V™ medium (Life Technologies, Carlsbad, CA)+5% human AB serum. IL-2 was not added to the medium. Four days after initiation, the live cells in each co-culture were counted with trypan blue for dead cell exclusion. Flow cytometry was then performed by staining T-cells with polyclonal biotin-labeled goat-anti-human BCMA antibodies (R&D Systems, Minneapolis, MN) followed by streptavidin (BD Biosciences, Franklin Lakes, NJ), anti-CD38 antibody (eBioscience, Inc., San Diego, CA), and anti-CD56 antibody (BD Biosciences, Franklin Lakes, NJ). Flow cytometry data analysis was performed by using FlowJo software (Tree Star, Inc., Ashland, OR).

Figure 7A:
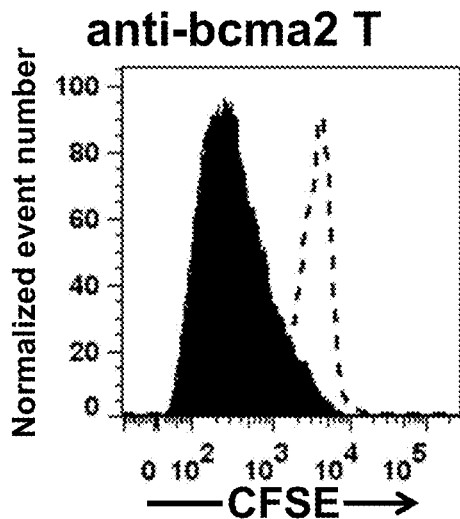
Figure 7B:
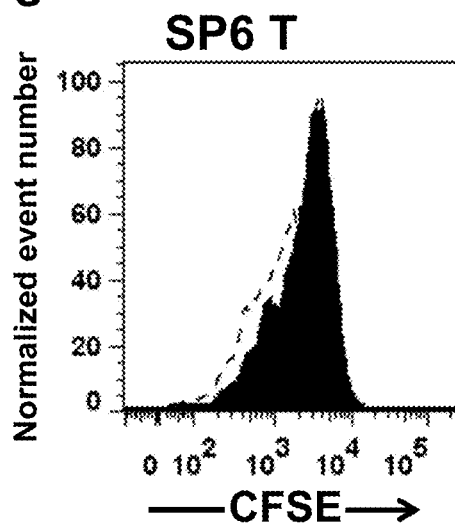

T-cells that expressed the anti-bcma2 CAR exhibited a greater dilution of CFSE when cultured with the BCMA-K562 cells than when cultured with negative control NGFR-K562 cells, as shown in FIG. 7A. These results indicate that T-cells transduced with the anti-bcma2 CAR specifically proliferated when stimulated with BCMA-expressing target cells. In contrast, there was no significant difference in CFSE dilution when T-cells expressing the SP6 CAR were cultured with either BCMA-K562 target cells or NGFR-K562 target cells (see FIG. 7B), which demonstrates a lack of BCMA-specific proliferation by T-cells expressing the SP6 CAR.

At the beginning of the proliferation assays, $0.8 \times 10^6$ T-cells expressing the anti-bcma2 CAR were cultured with either BCMA-K562 cells or NGFR-K562 cells. After 4 days of culture, $2.7 \times 10^6$ T-cells expressing the anti-bcma2 CAR were present in the cultures containing BCMA-K562 cells while only $0.6 \times 10^6$ T-cells expressing the anti-bcma2 CAR were present in the cultures containing NGFR-K562 cells. This BCMA-specific increase in the absolute number of T-cells expressing the anti-bcma2 CAR indicates that these T-cells proliferated in response to BCMA.

The results of this example demonstrate that T-cells expressing the inventive CAR exhibit BCMA-specific cytokine production, degranulation, and proliferation.

Example 4

This example demonstrates that T-cells expressing the inventive anti-BCMA CAR can destroy multiple myeloma cell lines.

Cytotoxicity assays were performed to determine whether T-cells transduced with the anti-bcma2 CAR described in Examples 2 and 3 could destroy BCMA-expressing multiple myeloma (MM) cell lines. Specifically, the cytotoxicity of target cells was measured by comparing the survival of BCMA-expressing target cells (i.e., multiple myeloma cell lines H929 and RPMI8226) relative to the survival of negative control CCRF-CEM cells using an assay described in, e.g., Kochenderfer et al., J. Immunotherapy, 32(7): 689-702 (2009), and Hermans et al., J. Immunological Methods, 285(1): 25-40 (2004).

Approximately 50,000 BCMA-expressing target cells and 50,000 CCRF-CEM cells were combined in the same tubes with different numbers of CAR-transduced T-cells. CCRF-CEM negative control cells were labeled with the fluorescent dye 5-(and-6)-(((4-chloromethyl)benzoyl)amino)tetramethylrhodamine (CMTMR) (Life Technologies, Carlsbad, CA), and BCMA-expressing target cells were labeled with CFSE. In all experiments, the cytotoxicity of effector T-cells that were transduced with the anti-bcma2 CAR was compared to the cytotoxicity of negative control effector T-cells from the same subject that were transduced with the SP6 CAR. Co-cultures were established in sterile 5 mL test tubes (BD Biosciences, Franklin Lakes, NJ) in duplicate at the following T-cell:target cell ratios: 20.0:1, 7:1, 2:1, and 0.7:1. The cultures were incubated for four hours at 37° C. Immediately after the incubation, 7-aminoactinomycin D (7AAD; BD Biosciences, Franklin Lakes, NJ) was added. The percentages of live BCMA-expressing target cells and live CCRF-CEM negative control cells were determined for each T-cell/target cell co-culture.

For each T-cell/target cell co-culture, the percent survival of BCMA-expressing target cells relative to the CCRF-CEM negative control cells was determined by dividing the percent BCMA-expressing cells by the percent CCRF-CEM negative control cells. The corrected percent survival of BCMA-expressing target cells was calculated by dividing the percent survival of BCMA-expressing target cells in each T-cell/target cell co-culture by the ratio of the percent BCMA-expressing target cells:percent CCRF-CEM negative control cells in tubes containing only BCMA-expressing target cells and CCRF-CEM negative control cells without effector T-cells. This correction was necessary to account for variation in the starting cell numbers and for spontaneous target cell death. Cytotoxicity was calculated as follows:

$$\% \text{ cytotoxicity of BCMA-expressing target cells} = 100 - \text{corrected } \% \text{ survival of BCMA-expressing target cells}$$

Figure 7C:
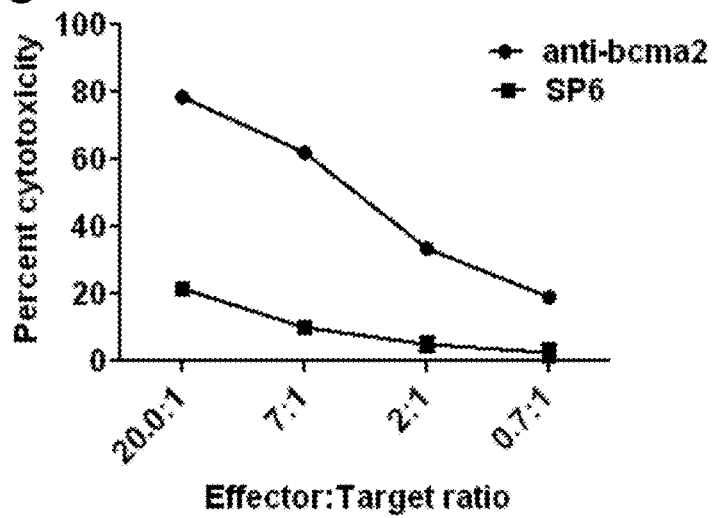
Figure 7D:
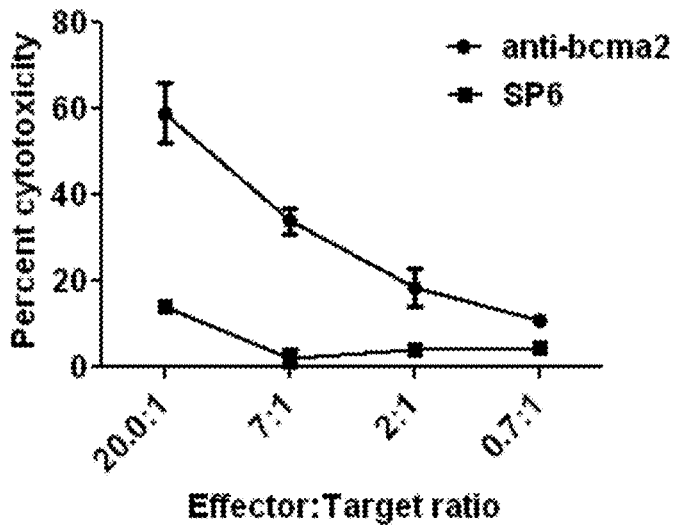

The results of the cytotoxicity assay are shown in FIGS. 7C and 7D. T-cells transduced with the anti-bcma2 CAR specifically killed the BCMA-expressing multiple myeloma cell lines H929 and RPMI8226. In contrast, T-cells transduced with the SP6 CAR exhibited much lower levels of cytotoxicity against these cell lines.

The results of this example demonstrate that the inventive nucleic acid sequence encoding an anti-BCMA CAR can be used in a method of destroying multiple myeloma cell lines.

Example 5

This example demonstrates that T-cells expressing the inventive anti-BCMA CAR can destroy primary multiple myeloma cells.

The primary multiple myeloma cells described in Example 2 were evaluated for BCMA expression, as well as BCMA-specific cytokine production, degranulation, and proliferation using the methods described above.

Cell surface BCMA expression was detected on four primary multiple myeloma samples, as well as on primary bone marrow multiple myeloma cells from Myeloma Patient 3 (see FIG. 8A). BCMA-expressing plasma cells made up 40% of the cells in the bone marrow sample from Myeloma Patient 3. Allogeneic T-cells transduced with the anti-bcma2 CAR from Donor C produced IFNγ after co-culture with the unmanipulated bone marrow cells of Myeloma Patient 3, as shown in FIG. 8B. Anti-bcma2 CAR-transduced T-cells from the same allogeneic donor produced much less IFNγ when they were cultured with peripheral blood mononuclear cell (PBMC) from Myeloma Patient 3. In addition, SP6-CAR-transduced T-cells from Donor C did not specifically recognize the bone marrow of Myeloma Patient 3. It has been previously reported that normal PBMC does not contain cells that express BCMA (see, e.g., Ng et al., *J. Immunology*, 173(2): 807-817 (2004)). To confirm this observation, PBMC of Patient 3 was assessed for BCMA expression by flow cytometry. PBMC of Patient 3 did not contain BCMA-expressing cells, aside from a small population of CD56+CD38$^{high}$ cells that made up approximately 0.75% of the PBMC. This population possibly consisted of circulating multiple myeloma cells.

A plasmacytoma resected from Myeloma Patient 1 consisted of 93% plasma cells, and these primary plasma cells expressed BCMA, as shown in FIG. 8C. T-cells from Myeloma Patient 2 produced IFNγ when cultured with the allogeneic, unmanipulated plasmacytoma cells of Myeloma Patient 1. T-cells from Myeloma Patient 2 did not produce significant amounts of IFNγ when cultured with PBMC from Myeloma patient 1. T-cells from Myeloma Patient 2 that were transduced with the SP6 CAR did not produce significant amounts of IFNγ when they were cultured with either plasmacytoma cells or PBMC from Myeloma Patient 1. The PBMC of Myeloma Patient 1 did not express BCMA as measured by flow cytometry.

T-cells of Myeloma Patient 1, who had received eight prior cycles of myeloma therapy, were successfully cultured and transduced with a lentivirus vector encoding the anti-bcma2 CAR. Eight days after the cultures were initiated, expression of the anti-bcma2 CAR was detected on 65% of the T-cells. The T-cells from Myeloma Patient 1 expressing the anti-bcma2 CAR produced IFNγ specifically in response to autologous plasmacytoma cells (FIG. 8D). T-cells from Myeloma Patient 1 expressing the SP6 CAR did not recognize autologous plasmacytoma cells. T-cells expressing the anti-bcma2 CAR and T-cells expressing the SP6 CAR did not recognize autologous PBMC. T-cells from Myeloma Patient 1 expressing the anti-bcma2 CAR also specifically killed autologous plasmacytoma cells at low effector to target ratios. In contrast, T-cells from Myeloma Patient 1 expressing the SP6 CAR exhibited low levels of cytotoxicity against autologous plasmacytoma cells (FIG. 8E).

The results of this example demonstrate that the inventive anti-BCMA CAR can be used in a method of destroying primary multiple myeloma cells.

Example 6

This example demonstrates that T-cells expressing the inventive anti-BCMA CARs can destroy established tumors in mice.

Immunodeficient NSG mice (NOD.Cg-Prkdcscid Il2rgtm1Wjl/SzJ, Jackson Laboratory) were injected intradermally with 8×10$^6$ RPMI8226 cells. Tumors were allowed to grow for 17 to 19 days, and then the mice received intravenous infusions of 8×10$^6$ human T-cells that were transduced with either the anti-bcma2 CAR or the SP6 CAR. Tumors were measured with calipers every 3 days. The longest length and the length perpendicular to the longest length were multiplied to obtain the tumor size (area) in mm$^2$. When the longest length reached 15 mm, mice were sacrificed. Animal studies were approved by the National Cancer Institute Animal Care and Use Committee.

The results of this example are shown in FIGS. 9A and 9B. At around day 6, mice treated with anti-bcma2-transduced T-cells showed a reduction in tumor size, and tumors were eradicated at day 15. In addition, all mice treated with anti-bcma2-transduced T-cells survived out to 30 days post T-cell infusion.

The results of this example demonstrate that the inventive anti-BMCA CAR can destroy multiple myeloma cells in vivo.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

SEQUENCE LISTING

```
Sequence total quantity: 12
SEQ ID NO: 1             moltype = DNA  length = 1512
FEATURE                  Location/Qualifiers
misc_feature             1..1512
                         note = Synthetic
source                   1..1512
                         mol_type = other DNA
                         organism = synthetic construct
SEQUENCE: 1
atggccctgc ctgtgacagc tctgctgctg cccctggccc tgctgctcca tgccgccaga   60
cccgacatcg tgctgaccca gagccccccc agcctggcca tgtctctggg caagagagcc  120
accatcagct gccgggccag cgagagcgtg accatcctgg gcagccacct gatctactgg  180
tatcagcaga agcctggcca gccccccacc ctgctgatcc agctggctag caatgtgcag  240
accggcgtgc ccgccagatt cagcggcagc ggcagcagaa ccgacttcac cctgaccatc  300
gaccccgtgg aagaggacga cgtggccgtg tactactgcc tgcagagccg gaccatcccc  360
cggaccttt g gcgaggaac aaagctggaa atcaagggca gcaccagcgg ctccggcaag  420
cctggctctg gcgagggcag cacaaaggga cagattcagc tggtgcagag cggccctgag  480
ctgaagaaac ccgcgagac agtgaagatc agctgcaagg cctccggcta caccttccgg  540
cactacagca tgaactgggt gaaacaggcc cctggcaagg gcctgaagtg gatgggccgg  600
atcaacaccc agagcggcgt gcccatctac gccgacgact tcaagggcag attcgccttc  660
agcgtggaaa ccagcgccag caccgcctac ctggtgatca acaacctgaa ggacgaggat  720
accgccagct acttctgcag caacgactac ctgtacagcc tggacttctg gggccagggc  780
accgccctga ccgtgtccag cttcgtgcct gtgttcctgc ccgccaagcc caccaccacc  840
cctgccccta gacctcccac cccagcccca caaatcgcca gccagcctct gtccctgcgg  900
cccgaagcct gtagacctgc tgccggcgga gccgtgcaca ccagaggcct ggatttcgcc  960
tgcgacatct acatctgggc ccctctggcc ggcacctgtg gcgtgctgct gctgagcctg 1020
gtgatcaccc tgtactgcaa ccaccggaac agaagcaagc ggagccggct gctgcacagc 1080
gactacatga acatgacccc aagacggcct ggcccaccc ggaagcacta ccagccttac 1140
gcccctccca gagacttcgc cgcctaccgg tccagagtga agttcagcag atccgccgac 1200
gcccctgcct accagcaggg acagaaccag ctgtacaacg agctgaacct gggcagacgg 1260
gaagagtacg acgtgctgga caagcggaga ggccgggacc ccgagatggg cggaaagccc 1320
agacggaaga accccagga aggcctgtat aacgaactgc agaaagacaa gatggccgag 1380
gcctacagcg agatcggcat gaagggcgag cggaggcgcg gcaagggcca cgatggcctg 1440
taccagggcc tgagcaccgc caccaaggac acctacgacg ccctgcacat gcaggccctg 1500
cccccccagat ga                                                    1512

SEQ ID NO: 2             moltype = DNA  length = 1512
FEATURE                  Location/Qualifiers
misc_feature             1..1512
                         note = Synthetic
source                   1..1512
                         mol_type = other DNA
                         organism = synthetic construct
SEQUENCE: 2
atggccctgc ctgtgacagc tctgctcctc cctctggccc tgctgctcca tgccgccaga   60
cccgacatcg tgctgaccca gagccccccc agcctggcca tgtctctggg caagagagcc  120
accatcagct gccgggccag cgagagcgtg accatcctgg gcagccacct gatccactgg  180
tatcagcaga agcccggcca gccccccacc ctgctgatcc agctgctgcag caatgtgcag  240
accggcgtgc ccgccagatt cagcggcagc ggcagcagaa ccgacttcac cctgaccatc  300
gaccccgtgg aagaggacga cgtggccgtg tactactgcc tgcagagccg gaccatcccc  360
cggaccttt g gcgaggcac caaactggaa atcaagggca gcaccagcgg ctccggcaag  420
cctggctctg gcgagggcag cacaaaggga cagattcagc tggtgcagag cggccctcac  480
ctgaagaaac ccgcgagac agtgaagatc agctgcaagg cctccggcta caccttcacc  540
gactacagca tcaactgggt gaaagagccc ctggcaagg gcctgaagtg gatgggctgg  600
atcaacaccg agacaagaga gcccgcctac gcctacgact ccggggcag attcgccttc  660
agcctggaaa ccagcgccag caccgcctac ctgcagatca caacctgaa gtacgaggac  720
accgccacct actttctgcg cctggactac agctacgcct ggactactgg gggccagggc  780
accagcgtga ccgtgtccag cttcgtgccc gtgttcctgc cgccaaacc taccaccacc  840
cctgccccta gacctcccac cccagcccca caaatcgcca gccagcctct gtctctgcgg  900
cccgaagcct gtagacctgc tgccggcgga gccgtgcaca ccagaggcct ggacttcgcc  960
tgcgacatct acatctgggc ccctctggcc ggcacctgtg gcgtgctgct gctgagcctg 1020
gtgatcaccc tgtactgcaa ccaccggaac agaagcaagc ggagccggct gctgcacagc 1080
gactacatga acatgacccc aagacggcct ggcccaccc ggaagcacta ccagccttac 1140
gcccctccca gagacttcgc cgcctaccgg tccagagtga agttcagcag atccgccgac 1200
gcccctgcct accagcaggg acagaaccag ctgtacaacg agctgaacct gggcagacgg 1260
gaagagtacg acgtgctgga caagcggaga ggccgggacc ccgagatggg cggaaagccc 1320
agacggaaga accccagga aggcctgtat aacgaactgc agaaagacaa gatggccgag 1380
gcctacagcg agatcggcat gaagggcgag cggaggcgcg gcaagggcca cgatggcctg 1440
taccagggcc tgagcaccgc caccaaggac acctacgacg ccctgcacat gcaggccctg 1500
cccccccagat ga                                                    1512

SEQ ID NO: 3             moltype = DNA  length = 1512
FEATURE                  Location/Qualifiers
misc_feature             1..1512
                         note = Synthetic
source                   1..1512
                         mol_type = other DNA
                         organism = synthetic construct
```

```
SEQUENCE: 3
atggctctgc ctgtgacagc tctgctgctg cctctggccc tgctgctgca tgccgccaga    60
cctgatatcg tgctgaccca gagccctccc agcctggcca tgtctctggg caagagagcc   120
accatcagct gcagagccag cgagagcgtg accatcctgg gcagccacct gatctactgg   180
tatcagcaga agcccggcca gccccccaca cctgctcttc agctggcctc caatgtgcag   240
accggcgtgc cagccagatt ttccggcagc ggcagcagaa ccgacttcac cctgaccatc   300
gaccccgtgg aagaggacga cgtggccgtg tactactgcc tgcagagcag aaccatcccc   360
cggacctttg gcgaggcac caagctggaa atcaagggca gcaccagcgg ctccggcaag   420
cctggatctg gcgaggggatc taccaaggga cagatccagc tggtgcagag cggccctgag   480
ctgaagaaac ccggcgagac agtgaagatc tcctgcaagg ccagcggcta caccttcacc   540
cactacagca tgaactgggt caagcaggcc cctggcaagg gcctgaagtg gatgggccgg   600
atcaacaccg agacaggcga gcccctgtac gccgacgact taagggcag attcgccttc   660
agcctggaaa ccagcgccag caccgcctac ctcgtgatca acaacctgaa gaacgaggac   720
accgccacct ttttctctc aacgactac tgtacagct gcgactactg ggggcagggc   780
accaccctga cagtgtctag cttcgtgccc gtgttcctgc ccgccaagcc tacaacaacc   840
cctgcccta gacctccac cccagcccct acaattgcct ctcagcctct gagcctgagg   900
cccgaggctt gtagaccagc tgctggcgga gccgtgcaca ccagaggact ggatttcgcc   960
tgcgacatct acatctgggc ccctctggcc ggcacctgtg gcgtgctgct gctgagcctg  1020
gtgatcaccc tgtactgcaa ccaccggaac agaagcaag ggagccggct gctgcacagc  1080
gactacatga acatgacccc aagacggcct ggccccaccc ggaagcacta ccagccttac  1140
gcccctccca gagacttcgc cgcctaccgg tccagagtga agttcagcag atccgccgac  1200
gcccctgcct accagcaggg acagaaccag ctgtacaacg agctgaacct gggcagacgg  1260
gaagagtacg acgtgctgga caagcggaga ggccgggacc ccgagatggg cggaaagccc  1320
agacggaaga accccaggga aggcctgtat aacgaactgc agaaagacaa gatggccgag  1380
gcctacagcg agatcggcat gaagggcgag cggaggcgcg gcaagggcca cgatggcctg  1440
taccagggcc tgagcaccgc caccaaggac acctacgacg ccctgcacat gcaggccctg  1500
ccccccagat ga                                                     1512

SEQ ID NO: 4         moltype = AA  length = 503
FEATURE              Location/Qualifiers
REGION               1..503
                     note = Synthetic
source               1..503
                     mol_type = protein
                     organism = synthetic construct
SEQUENCE: 4
MALPVTALLL PLALLLHAAR PDIVLTQSPP SLAMSLGKRA TISCRASESV TILGSHLIYW    60
YQQKPGQPPT LLIQLASNVQ TGVPARFSGS GSRTDFTLTI DPVEEDDVAV YYCLQSRTIP   120
RTFGGGTKLE IKGSTSGSGK PGSGEGSTKG QIQLVQSGPE LKKPGETVKI SCKASGYTFR   180
HYSMNWVKQA PGKGLKWMGR INTESGVPIY ADDFKGRFAF SVETSASTAY LVINNLKDED   240
TASYFCSNDY LYSLDFWGQG TALTVSSFVP VFLPAKPTTT PAPRPPTPAP TIASQPLSLR   300
PEACRPAAGG AVHTRGLDFA CDIYIWAPLA GTCGVLLLSL VITLYCNHRN RSKRSRLLHS   360
DYMNMTPRRP GPTRKHYQPY APPRDFAAYR SRVKFSRSAD APAYQQGNQ LYNELNLGRR   420
EEYDVLDKRR GRDPEMGGKP RRKNPQEGLY NELQKDKMAE AYSEIGMKGE RRRGKGHDGL   480
YQGLSTATKD TYDALHMQAL PPR                                           503

SEQ ID NO: 5         moltype = AA  length = 503
FEATURE              Location/Qualifiers
REGION               1..503
                     note = Synthetic
source               1..503
                     mol_type = protein
                     organism = synthetic construct
SEQUENCE: 5
MALPVTALLL PLALLLHAAR PDIVLTQSPP SLAMSLGKRA TISCRASESV TILGSHLIHW    60
YQQKPGQPPT LLIQLASNVQ TGVPARFSGS GSRTDFTLTI DPVEEDDVAV YYCLQSRTIP   120
RTFGGGTKLE IKGSTSGSGK PGSGEGSTKG QIQLVQSGPE LKKPGETVKI SCKASGYTFT   180
DYSINWVKRA PGKGLKWMGW INTETREPAY AYDFRGRFAF SLETSASTAY LQINNLKYED   240
TATYFCALDY SYAMDYWGQG TSVTVSSFVP VFLPAKPTTT PAPRPPTPAP TIASQPLSLR   300
PEACRPAAGG AVHTRGLDFA CDIYIWAPLA GTCGVLLLSL VITLYCNHRN RSKRSRLLHS   360
DYMNMTPRRP GPTRKHYQPY APPRDFAAYR SRVKFSRSAD APAYQQGNQ LYNELNLGRR   420
EEYDVLDKRR GRDPEMGGKP RRKNPQEGLY NELQKDKMAE AYSEIGMKGE RRRGKGHDGL   480
YQGLSTATKD TYDALHMQAL PPR                                           503

SEQ ID NO: 6         moltype = AA  length = 503
FEATURE              Location/Qualifiers
REGION               1..503
                     note = Synthetic
source               1..503
                     mol_type = protein
                     organism = synthetic construct
SEQUENCE: 6
MALPVTALLL PLALLLHAAR PDIVLTQSPP SLAMSLGKRA TISCRASESV TILGSHLIYW    60
YQQKPGQPPT LLIQLASNVQ TGVPARFSGS GSRTDFTLTI DPVEEDDVAV YYCLQSRTIP   120
RTFGGGTKLE IKGSTSGSGK PGSGEGSTKG QIQLVQSGPE LKKPGETVKI SCKASGYTFT   180
HYSMNWVKQA PGKGLKWMGR INTEGEPLY ADDFKGRFAF SLETSASTAY LVINNLKNED   240
TATFFCSNDY LYSCDYWGQG TTLTVSSFVP VFLPAKPTTT PAPRPPTPAP TIASQPLSLR   300
PEACRPAAGG AVHTRGLDFA CDIYIWAPLA GTCGVLLLSL VITLYCNHRN RSKRSRLLHS   360
DYMNMTPRRP GPTRKHYQPY APPRDFAAYR SRVKFSRSAD APAYQQGNQ LYNELNLGRR   420
```

```
EEYDVLDKRR GRDPEMGGKP RRKNPQEGLY NELQKDKMAE AYSEIGMKGE RRRGKGHDGL    480
YQGLSTATKD TYDALHMQAL PPR                                           503

SEQ ID NO: 7            moltype = AA  length = 18
FEATURE                 Location/Qualifiers
REGION                  1..18
                        note = Synthetic
source                  1..18
                        mol_type = protein
                        organism = synthetic construct
SEQUENCE: 7
GSTSGSGKPG SGEGSTKG                                                 18

SEQ ID NO: 8            moltype = AA  length = 507
FEATURE                 Location/Qualifiers
REGION                  1..507
                        note = Synthetic
source                  1..507
                        mol_type = protein
                        organism = synthetic construct
SEQUENCE: 8
MLLLVTSLLL CELPHPAFLL IPDIVLTQSP PSLAMSLGKR ATISCRASES VTILGSHLIH    60
WYQQKPGQPP TLLIQLASNV QTGVPARFSG SGSRTDFTLT IDPVEEDDVA VYYCLQSRTI   120
PRTFGGGTKL EIKGSTSGSG KPGSGEGSTK GQIQLVQSGP ELKKPGETVK ISCKASGYTF   180
TDYSINWVKR APGKGLKWMG WINTETREPA YAYDFRGRFA FSLETSASTA YLQINNLKYE   240
DTATYFCALD YSYAMDYWGQ GTSVTVSSAA AFVPVFLPAK PTTTPAPRPP TPAPTIASQP   300
LSLRPEACRP AAGGAVHTRG LDFACDIYIW APLAGTCGVL LLSLVITLYC NHRNRSKRSR   360
LLHSDYMNMT PRRPGPTRKH YQPYAPPRDF AAYRSRVKFS RSADAPAYQQ GQNQLYNELN   420
LGRREEYDVL DKRRGRDPEM GGKPRRKNPQ EGLYNELQKD KMAEAYSEIG MKGERRRGKG   480
HDGLYQGLST ATKDTYDALH MQALPPR                                      507

SEQ ID NO: 9            moltype = AA  length = 506
FEATURE                 Location/Qualifiers
REGION                  1..506
                        note = Synthetic
source                  1..506
                        mol_type = protein
                        organism = synthetic construct
SEQUENCE: 9
MALPVTALLL PLALLLHAAR PDIVLTQSPP SLAMSLGKRA TISCRASESV TILGSHLIHW    60
YQQKPGQPPT LLIQLASNVQ TGVPARFSGS GSRTDFTLTI DPVEEDDVAV YYCLQSRTIP   120
RTFGGGTKLE IKGSTSGSGK PGSGEGSTKG QIQLVQSGPE LKKPGETVKI SCKASGYTFT   180
DYSINWVKRA PGKGLKWMGW INTETREPAY AYDFRGRFAF SLETSASTAY LQINNLKYED   240
TATYFCALDY SYAMDYWGQG TSVTVSSAAA FVPVFLPAKP TTTPAPRPPT PAPTIASQPL   300
SLRPEACRPA AGGAVHTRGL DFACDIYIWA PLAGTCGVLL LSLVITLYCN HRNRSKRSRL   360
LHSDYMNMTP RRPGPTRKHY QPYAPPRDFA AYRSRVKFSR SADAPAYQQG QNQLYNELNL   420
GRREEYDVLD KRRGRDPEMG GKPRRKNPQE GLYNELQKDK MAEAYSEIGM KGERRRGKGH   480
DGLYQGLSTA TKDTYDALHM QALPPR                                       506

SEQ ID NO: 10           moltype = AA  length = 512
FEATURE                 Location/Qualifiers
REGION                  1..512
                        note = Synthetic
source                  1..512
                        mol_type = protein
                        organism = synthetic construct
SEQUENCE: 10
MALPVTALLL PLALLLHAAR PDIVLTQSPP SLAMSLGKRA TISCRASESV TILGSHLIHW    60
YQQKPGQPPT LLIQLASNVQ TGVPARFSGS GSRTDFTLTI DPVEEDDVAV YYCLQSRTIP   120
RTFGGGTKLE IKGSTSGSGK PGSGEGSTKG QIQLVQSGPE LKKPGETVKI SCKASGYTFT   180
DYSINWVKRA PGKGLKWMGW INTETREPAY AYDFRGRFAF SLETSASTAY LQINNLKYED   240
TATYFCALDY SYAMDYWGQG TSVTVSSAAA FVPVFLPAKP TTTPAPRPPT PAPTIASQPL   300
SLRPEACRPA AGGAVHTRGL DFACDIYIWA PLAGTCGVLL LSLVITLYCN HRNRFSVVKR   360
GRKKLLYIFK QPFMRPVQTT QEEDGCSCRF PEEEEGGCEL RVKFSRSADA PAYQQGQNQL   420
YNELNLGRRE EYDVLDKRRG RDPEMGGKPR RKNPQEGLYN ELQKDKMAEA YSEIGMKGER   480
RRGKGHDGLY QGLSTATKDT YDALHMQALP PR                                512

SEQ ID NO: 11           moltype = AA  length = 502
FEATURE                 Location/Qualifiers
REGION                  1..502
                        note = Synthetic
source                  1..502
                        mol_type = protein
                        organism = synthetic construct
SEQUENCE: 11
MALPVTALLL PLALLLHAAR PDIVLTQSPP SLAMSLGKRA TISCRASESV TILGSHLIHW    60
YQQKPGQPPT LLIQLASNVQ TGVPARFSGS GSRTDFTLTI DPVEEDDVAV YYCLQSRTIP   120
RTFGGGTKLE IKGSTSGSGK PGSGEGSTKG QIQLVQSGPE LKKPGETVKI SCKASGYTFT   180
DYSINWVKRA PGKGLKWMGW INTETREPAY AYDFRGRFAF SLETSASTAY LQINNLKYED   240
```

-continued

```
TATYFCALDY SYAMDYWGQG TSVTVSSAAA FVPVFLPAKP TTTPAPRPPT PAPTIASQPL   300
SLRPEACRPA AGGAVHTRGL DFACDIYIWA PLAGTCGVLL LSLVITLYCN HRNRRDQRLP   360
PDAHKPPGGG SFRTPIQEEQ ADAHSTLAKI RVKFSRSADA PAYQQGQNQL YNELNLGRRE   420
EYDVLDKRRG RDPEMGGKPR RKNPQEGLYN ELQKDKMAEA YSEIGMKGER RRGKGHDGLY   480
QGLSTATKDT YDALHMQALP PR                                            502

SEQ ID NO: 12          moltype = AA  length = 549
FEATURE                Location/Qualifiers
REGION                 1..549
                       note = Synthetic
source                 1..549
                       mol_type = protein
                       organism = synthetic construct
SEQUENCE: 12
MALPVTALLL PLALLLHAAR PDIVLTQSPP SLAMSLGKRA TISCRASESV TILGSHLIHW    60
YQQKPGQPPT LLIQLASNVQ TGVPARFSGS GSRTDFTLTI DPVEEDDVAV YYCLQSRTIP   120
RTFGGGTKLE IKGSTSGSGK PGSGEGSTKG QIQLVQSGPE LKKPGETVKI SCKASGYTFT   180
DYSINWVKRA PGKGLKWMGW INTETREPAY AYDFRGRFAF SLETSASTAY LQINNLKYED   240
TATYFCALDY SYAMDYWGQG TSVTVSSAAA FVPVFLPAKP TTTPAPRPPT PAPTIASQPL   300
SLRPEACRPA AGGAVHTRGL DFACDIYIWA PLAGTCGVLL LSLVITLYCN HRNRFSVVKR   360
GRKKLLYIFK QPFMRPVQTT QEEDGCSCRF PEEEEGGCEL RRDQRLPPDA HKPPGGGSFR   420
TPIQEEQADA HSTLAKIRVK FSRSADAPAY QQGQNQLYNE LNLGRREEYD VLDKRRGRDP   480
EMGGKPRRKN PQEGLYNELQ KDKMAEAYSE IGMKGERRRG KGHDGLYQGL STATKDTYDA   540
LHMQALPPR                                                          549
```

The invention claimed is:

1. A method of treating multiple myeloma in a human subject, the method comprising administering to the human subject a pharmaceutical composition comprising a population of human T cells, wherein the T cells comprise a nucleic acid that encodes a chimeric antigen receptor (CAR) comprising:
    (a) an antigen recognition moiety that binds human B-Cell Maturation Antigen (BCMA);
    (b) a CD8α hinge domain;
    (c) a CD8α transmembrane domain;
    (d) a 4-1BB intracellular T cell signaling domain; and
    (e) a CD3ζ intracellular T cell signaling domain.

2. The method of claim 1, wherein the antigen recognition moiety is an antigen binding portion of an antibody.

3. The method of claim 1, wherein the antigen recognition moiety comprises a variable region.

4. The method of claim 1, wherein the antigen recognition moiety comprises two variable regions.

5. The method of claim 3, wherein the antigen recognition moiety comprises a heavy chain variable (VH) region.

6. The method of claim 1, wherein the antigen recognition moiety comprises a complementarity determining region (CDR)1, a CDR2 and a CDR3.

7. The method of claim 5, wherein the VH region comprises VH CDR1, VH CDR2 and VH CDR3.

8. The method of claim 4, wherein each of the variable regions comprises a CDR1, CDR2 and CDR3.

9. The method of claim 1, wherein the CAR further comprises a signal sequence.

10. The method of claim 9, wherein the signal sequence is a CD8α signal sequence.

11. The method of claim 1, wherein the CD3ζ intracellular T cell signaling domain comprises the CD3ζ intracellular T cell signaling domain in SEQ ID NO: 10.

12. The method of claim 1, wherein the 4-1BB intracellular T cell signaling domain comprises the 4-1BB intracellular T cell signaling domain in SEQ ID NO: 10.

13. The method of claim 1, wherein the CD3ζ intracellular T cell signaling domain comprises the CD3ζ intracellular T cell signaling domain in SEQ ID NO: 10 and the 4-1BB intracellular T cell signaling domain comprises the 4-1BB intracellular T cell signaling domain in SEQ ID NO: 10.

14. The method of claim 1, wherein the CD8α transmembrane domain is the CD8α transmembrane domain of SEQ ID NO: 10.

15. The method of claim 1, wherein the CD3ζ intracellular T cell signaling domain comprises the CD3ζ intracellular T cell signaling domain in SEQ ID NO: 10; the 4-1BB intracellular T cell signaling domain comprises the 4-1BB intracellular T cell signaling domain in SEQ ID NO: 10 and the CD8α transmembrane domain is the CD8α transmembrane domain of SEQ ID NO: 10.

16. The method of claim 10, wherein the signal sequence is the CD8α signal sequence of SEQ ID NO: 10.

17. The method of claim 9, wherein the CD3ζ intracellular T cell signaling domain comprises the CD3ζ intracellular T cell signaling domain in SEQ ID NO: 10; the 4-1BB intracellular T cell signaling domain comprises the 4-1BB intracellular T cell signaling domain in SEQ ID NO: 10; the CD8α transmembrane domain is the CD8α transmembrane domain of SEQ ID NO: 10 and the signal sequence is the CD8α signal sequence of SEQ ID NO: 10.

18. The method of claim 1, wherein the population of human T cells is from the human subject.

* * * * *